United States Patent
Downey et al.

(10) Patent No.: US 11,568,955 B2
(45) Date of Patent: Jan. 31, 2023

(54) PROCESS FOR CREATING REFERENCE DATA FOR PREDICTING CONCENTRATIONS OF QUALITY ATTRIBUTES

(71) Applicant: LONZA LTD, Visp (CH)

(72) Inventors: Brandon John Downey, Bend, OR (US); John Michael Schmitt, Bend, OR (US); Jeffrey Francis Breit, Visp (CH)

(73) Assignee: LONZA LTD, Visp (CH)

( * ) Notice: Subject to any disclaimer, the term of this patent is extended or adjusted under 35 U.S.C. 154(b) by 748 days.

(21) Appl. No.: 16/546,843

(22) Filed: Aug. 21, 2019

(65) Prior Publication Data
US 2020/0066369 A1   Feb. 27, 2020

Related U.S. Application Data

(60) Provisional application No. 62/720,309, filed on Aug. 21, 2018.

(51) Int. Cl.
*G16B 5/00* (2019.01)
*C12M 1/26* (2006.01)
(Continued)

(52) U.S. Cl.
CPC ............... *G16B 5/00* (2019.02); *B01L 3/502* (2013.01); *C12M 29/10* (2013.01); *C12M 33/00* (2013.01);
(Continued)

(58) Field of Classification Search
CPC ........ G16B 5/00; G16B 13/048; G16B 40/00; B01L 3/502; B01L 2400/082;
(Continued)

(56) References Cited

U.S. PATENT DOCUMENTS

| | | |
|---|---|---|
| 5,656,491 A | 8/1997 | Cassani et al. |
| 6,051,389 A | 4/2000 | Ahl et al. |

(Continued)

FOREIGN PATENT DOCUMENTS

| | | |
|---|---|---|
| WO | WO2006/065918 | 6/2006 |
| WO | WO2018/115161 | 6/2018 |

OTHER PUBLICATIONS

Zupke, et al. Real-Time Product Attribute Control to Manufacture Antibodies with Defined N-Linked Glycan Levels, American Institute of Chemical Engineers 2015, Biotechnol. Prog. 2015, vol. 31, No. 5, pp. 1433-1441.

(Continued)

*Primary Examiner* — Michael L Hobbs
(74) *Attorney, Agent, or Firm* — Medler Ferro Woodhouse & Mills PLLC

(57) ABSTRACT

A process and system for efficiently producing reference data that can be fed into a predictive model for predicting quality attribute concentrations in cell culture processes. A perfusion bioreactor is operated at pseudo-steady-state conditions and one or more attribute influencing parameters are manipulated and changed over time. As the one or more attribute influencing parameters are manipulated, one or more quality attributes are monitored and measured. In one embodiment, multiple quality attributes are monitored and measured in parallel. The quality attribute information is recorded in conjunction with the changes in the attribute influencing parameters. This information is then fed to the predictive model for propagating cell cultures in commercial processes and maintaining the cell cultures within desired preset limits.

32 Claims, 6 Drawing Sheets

(51) Int. Cl.
*B01L 3/00* (2006.01)
*G16B 40/00* (2019.01)
*C12N 5/071* (2010.01)
*C12M 1/34* (2006.01)
*G05B 13/04* (2006.01)
*C12M 1/00* (2006.01)

(52) U.S. Cl.
CPC ............ *C12M 41/12* (2013.01); *C12M 41/26* (2013.01); *C12M 41/32* (2013.01); *C12M 41/34* (2013.01); *C12M 41/36* (2013.01); *C12M 41/38* (2013.01); *C12N 5/0602* (2013.01); *G05B 13/048* (2013.01); *G16B 40/00* (2019.02); *B01L 2300/0867* (2013.01); *B01L 2400/082* (2013.01)

(58) Field of Classification Search
CPC ........... B01L 2300/0867; C12M 29/10; C12M 33/00; C12M 41/12; C12M 41/26; C12M 41/32; C12M 41/34; C12M 41/36; C12M 41/38; C12M 41/48; C12N 5/0602
See application file for complete search history.

(56) References Cited

U.S. PATENT DOCUMENTS

| | | |
|---|---|---|
| 7,629,167 B2 | 12/2009 | Hodge et al. |
| 8,298,054 B2 | 10/2012 | Hodge et al. |
| 8,318,416 B2 | 11/2012 | Tsang et al. |
| 8,753,871 B2 | 6/2014 | West |
| 9,783,774 B2 | 10/2017 | Namatame et al. |
| 2006/0019388 A1 | 1/2006 | Hutmacher et al. |
| 2009/0104594 A1 | 4/2009 | Webb |
| 2009/0305626 A1 | 12/2009 | Hope |
| 2011/0280797 A1 | 11/2011 | Mohtadi et al. |
| 2012/0077429 A1 | 3/2012 | Wernimont et al. |
| 2013/0245830 A1* | 9/2013 | West ........................ C12Q 3/00 700/266 |
| 2013/0280797 A1 | 10/2013 | Rao et al. |
| 2014/0163340 A1 | 6/2014 | Say |
| 2014/0295532 A1 | 10/2014 | Ray et al. |
| 2015/0329817 A1* | 11/2015 | Namatame ............. C12M 41/00 435/286.1 |
| 2017/0130186 A1 | 5/2017 | Berry et al. |
| 2017/0238856 A1 | 8/2017 | Botvinick et al. |
| 2017/0283505 A1 | 10/2017 | Gawlitzek et al. |
| 2018/0087079 A1* | 3/2018 | Du .......................... C12P 21/00 |

OTHER PUBLICATIONS

Qin et al., A Survey of Industrial Model Predictive Control Technology, Control Engineering Practice 11, (2003) pp. 733-764.

Huong Le, et al., Multivariate Analysis of Cell Culture Bioprocess data-Lactate Consumption as Process Indicator, Journal of Biotechnology 162 (2012) 210-223.

Brandon Downey, et al., A System Identification Approach for Developing Model Predictive Controllers of Antibody Quality Attributes in Cell Culture Processes, 2017, The Authors Biotechnology Progress published by Wiley Periodicals, Inc. on behalf of American Institute of Chemical Engineers, pp. 1-15.

Wolfgang Sommeregger et al., Quality By Control: Towards Model Predictive Control of Mammalian Cell Culture Bioprocesses, Biotechnology Journal., 2017, 1600546, 1 of 7.

Dowd et al., Optimization and Control of Perfusion Cultures Using a Viable Cell Probe and Cell Specific Perfusion Rates, Springer Cytotechnology, May 2003, 42(1): 35-45, https://www.ncbi.nih.gov/pmc/articles/PMC3449505.

PCT/US2019/047484 International Search Report and Written Opinion, dated Nov. 21, 2019, 12 pages.

* cited by examiner

PROCESS FOR CREATING REFERENCE DATA FOR PREDICTING CONCENTRATIONS OF QUALITY ATTRIBUTES

RELATED APPLICATIONS

The present application is based on and claims priority to U.S. Provisional Patent application Ser. No. 62/720,309, filed on Aug. 21, 2018, which is incorporated herein by reference.

BACKGROUND

Bioreactors, which are apparatuses in which biological reactions or processes can be carried out on a laboratory or industrial scale, are used widely within the biopharmaceutical industry. Bioreactors can be used to produce all different types of bioproducts. Bioproducts can include, for instance, cell cultures and materials derived from cell cultures including beverages, biofuels, bioenergy, biochemicals, antibiotics, amino acids, enzymes, monoclonal antibodies, monomers, proteins, food cultures, biopolymers, alcohols, flavorings, fragrances, and the like. In some embodiments, cell cultures can be grown for cell therapy. Cell therapy is the prevention, treatment, cure or mitigation of disease or injuries in humans by the administration of autologous, allogeneic or xenogeneic cells that have been manipulated or altered ex vivo. One goal of cell therapy is to repair, replace or restore damaged tissues or organs.

Cell cultures are typically grown in batch processes where the biological material remains in the bioreactor until the end of the reaction time. In certain of these processes, fluid medium contained within the bioreactor can be periodically or continuously removed and resupplied in order to replenish nutrients contained within the fluid medium and for possibly removing damaging by-products that are produced during the process.

During the growth of cell cultures, the regulation of key components, such as metabolites in the medium can have a direct impact on the quality of the product that is produced. Product quality is subject to process disturbances. These process disturbances themselves are very difficult to prevent. For example, metabolic behavior of cells can often drastically change with small unmeasured changes in cell culture media raw materials. Since the source of this variation is difficult to prevent, and its effect on the product quality is often poorly understood, it is desirable to have the ability to directly control product quality, such that consistent product quality is obtained despite the presence of these disturbances.

Historically, bioprocesses have been monitored by removing samples that are then analyzed for one or more quality attributes. Should a particular quality attribute be outside desired limits, various different controls may be implemented in order to influence the behavior of the quality attribute in the cell culture. Unfortunately, however, many problems are identified too late in the process to enact successful remedial action.

Recently, those skilled in the art have attempted to design predictive control models in order to control one or more quality attributes in a cell culture. An overview of commercially available model predictive control technology, for instance, is disclosed in an article entitled "A survey of industrial model predictive control technology" by Quin et al., which is incorporated herein by reference. Zupke et al., published an article entitled "Real-time product attribute control to manufacture antibodies with defined N-linked Glycan levels" and discusses using nonlinear model predictive control. Sommeregger et al., published an article entitled "Quality by control: towards model predictive control of mammalian cell culture bioprocesses" which is directed to implementing process analytical technology to move to a more flexible quality design approach.

Various problems have been experienced in designing predictive models. For instance, most predictive models are developed and based upon historical data collected from previous cell cultures. Unfortunately, however, in some applications, the historical data is insufficient to provide accurate predictive control and/or the historical data is not reliable due to various anomalies that may occur in any individual cell culture. Another limitation, often encountered in bioprocessing when manual sampling and analysis is performed, is that the sampling frequency of attribute influencing parameters and quality attributes is insufficient to develop the dynamic model required by a control strategy. In such instances, one knows where one started and where one wound up, but don't have enough resolution into the path taken to get there (from which one could determine the dynamics of the system). Developing a functional control system requires developing a model that can accurately determine the path of the quality attributes, given the paths of the attribute influencing parameters. Thus, in order to improve the quality in predictive models, a need exists for a system and method of producing reference data that may be used in predictive models. For example, a need exists for a method of producing reference data for predictive models wherein the reference data is reliable, improves the predictive model performance and/or can be obtained efficiently and in a relatively short period of time.

SUMMARY

In general, the present disclosure is directed to a method and system for developing controllers of at least one quality attribute in a cell culture. For instance, the method and system can be used to develop model predictive controllers in cell culture systems that that are designed to predict quality attribute quantities during processing. The system and method of the present disclosure, however, can be used in various other processes. For instance, in general, the process and system of the disclosure can be used for the development of a dynamic/predictive model to function in a whole host of other control strategies.

In one embodiment, the present disclosure is directed to an efficient and reliable method for generating reference data that may be incorporated into a predictive controller for controlling one or more quality attributes in a cell culture. For example, in one embodiment, the present disclosure is directed to a perfusion bioreactor system and method that runs relatively short cell culture cycles for generating reference data for multiple quality attributes in parallel.

For example, in one embodiment, the present disclosure is directed to a process for creating reference data for predicting quantities, such as concentrations, of quality attributes in a cell culture. The process includes the steps of introducing a cell culture into a perfusion bioreactor. A nutrient media is fed to the perfusion bioreactor and fluid media is withdrawn from the perfusion bioreactor so as to maintain a fluid media volume in the perfusion bioreactor within preset limits. For instance, in one embodiment, the fluid media volume remains relatively constant, such as within 5% of a desired volume level. In accordance with the present disclosure, at least a first attribute influencing parameter is controlled and/or fed into the perfusion bioreactor. The first attribute influencing parameter is related to or has an impact on at least a first quality attribute in the cell culture. The first attribute influencing parameter is varied in the perfusion bioreactor over time. For example, in one embodiment, the concentration of the first attribute influencing parameter can vary over time. As the first attribute influencing parameter is changed, a quantity of the first quality attribute is determined over the same period of time in the cell culture. The quantity of the first quality attribute that is determined can be a concentration, a mass change, a ratio, a percent change, or the like. In addition, and in parallel, a quantity of a second quality attribute is also determined over time in a cell culture as the at least one attribute influencing parameter is changed. The quality attribute data that is generated during the process can then be used as reference data and inputted into a predictive model. For example, the reference data can be collected in a manner so that the reference data is configured to be inputted into a controller that predicts future quantities of the quality attribute over time. The phase "configured to be inputted" refers to the fact that the reference data is collected and then can be transferred to a predictive model using any suitable means, such as through a web-based communication, through using an electronic memory, such as a flash drive, a computer disk, or the like, or can be transmitted to the predictive model through other means of data transmission whether the data is transmitted manually or through automatic means. The predictive model, for instance, can be configured to determine a future concentration of the quality attribute in a new cell culture, such as a cell culture grown in a batch process.

For instance, in one embodiment, during the growth of a cell culture, the first and second quality attribute quantities can be measured and fed to a controller. The controller can include a predictive model that determines a future quantity, such as concentration, of the quality attributes in the cell culture based in part on the reference data generated in the perfusion bioreactor. At least one condition within the cell culture can then be selectively changed based upon the determined future concentration of the quality attributes in the cell culture for maintaining the concentration of the quality attributes within preset limits.

In one embodiment, more than one attribute influencing parameter can be controlled and/or fed into the perfusion bioreactor and varied over time. For example, in one embodiment, a first attribute influencing parameter and a second attribute influencing parameter can be fed to the perfusion bioreactor simultaneously. The first attribute influencing parameter can be related to or have an impact on the first quality attribute while the second attribute influencing parameter can be related to or have an impact on the second quality attribute in the cell culture. The first and second influencing parameters can be varied simultaneously within the perfusion bioreactor for obtaining data regarding the first quality attribute and the second quality attribute in parallel. In other embodiments, more than two quality attributes can be monitored during the perfusion bioreactor process.

In other embodiments, a plurality of attribute influencing parameters can be manipulated within the perfusion bioreactor. The plurality of attribute influencing parameters can have an effect on a plurality of quality attributes. For large systems with many quality attributes and attribute influencing parameters, machine learning/system identification can be used to spot trends and develop a dynamic model that can be used in a predictive controller.

In one embodiment, multiple attribute influencing parameters can impact the same quality attribute in different ways and vice versa. Through the process and system of the present disclosure, a recipe can be generated for each attribute influencing parameter in order to obtain reliable information regarding their effects on the various quality attributes. This reference data can then be inputted into a predictive controller that determines how to vary each of the attribute influencing parameters to achieve the best performance with respect to the quality attribute.

Of particular advantage, the quality attribute data collected from the perfusion bioreactor can be created and obtained efficiently and over a relatively small amount of time. For instance, the quality attribute data can be obtained from the perfusion bioreactor in a time period of less than about 48 hours, such as in a time period of less than about 30 hours.

During operation of the perfusion bioreactor, the at least one attribute influencing parameter can be varied using different methods and techniques. In one embodiment, for instance, each attribute influencing parameter can be changed in a step wise manner. In one embodiment, a step wise change in the attribute influencing parameter is made and information related to one or more quality attributes can be collected until steady state is obtained within the perfusion bioreactor. In an alternative embodiment, however, step wise changes are made to the attribute influencing parameters and data related to one or more quality attributes are collected before steady state is obtained and a further step wise change is made in at least one of the attribute influencing parameters.

In addition to manipulating the attribute influencing parameters in a step wise manner, the attribute influencing parameters can also be changed in various ways. For instance, the attribute influencing parameters can be changed in a nonlinear manner, such as according to a sinusoidal pattern. Alternatively, an attribute influencing parameter can be gradually increased or ramped up and/or can be gradually decreased or ramped down within the perfusion bioreactor.

The present disclosure is also directed to a system for creating reference data used for predicting quality attribute values in a cell culture. The system includes a perfusion bioreactor. A plurality of parameter feeds are placed in fluid communication with the perfusion bioreactor. Each parameter feed is for feeding an attribute influencing parameter to the perfusion bioreactor. In accordance with the present disclosure, an input controller is placed in communication with at least one of the parameter feeds. The input controller is configured to manipulate a quantity of at least one attribute influencing parameter being fed to the perfusion bioreactor so that the attribute influencing parameter varies over time within the perfusion bioreactor in a controlled manner.

The system further includes at least one sample collection subsystem that obtains samples from the perfusion bioreactor and analyzes the samples for at least one quality attribute. The at least one sample collection subsystem is configured to collect samples in order to monitor changes in the quality attribute as the quantity of the attribute influencing parameter varies over time in the perfusion bioreactor. In one embodiment, the at least one sample collection subsystem is automated so that samples are automatically collected from the perfusion bioreactor and analyzed.

In accordance with the present disclosure, the monitored changes in the at least one quality attribute in relation to the manipulated changes in the at least one attribute influencing parameter comprise reference data. The system further includes a system database that receives and stores the reference data in a media configured to transfer the reference data to a controller of a cell culture system.

In one embodiment, the system includes a plurality of perfusion bioreactors as described above. One or more input controllers can be configured to control at least one parameter feed for each of the multiple perfusion bioreactors in order to manipulate a quantity of at least one attribute influencing parameter being fed to each of the perfusion bioreactors. In this manner, reference data can be obtained from multiple perfusion bioreactors simultaneously and in parallel. In one embodiment, the same attribute influencing parameter can be varied in multiple perfusion bioreactors according to preset recipes. For instance, the attribute influencing parameter can be manipulated in a different way within each of the perfusion bioreactors so that the attribute influencing parameter changes over time in each of the perfusion bioreactors in a different manner. By monitoring one or more quality attributes, dynamic information can be received and collected regarding how the one or more quality attributes change as the attribute influencing parameter is changed according to the different recipes.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Figure 1:
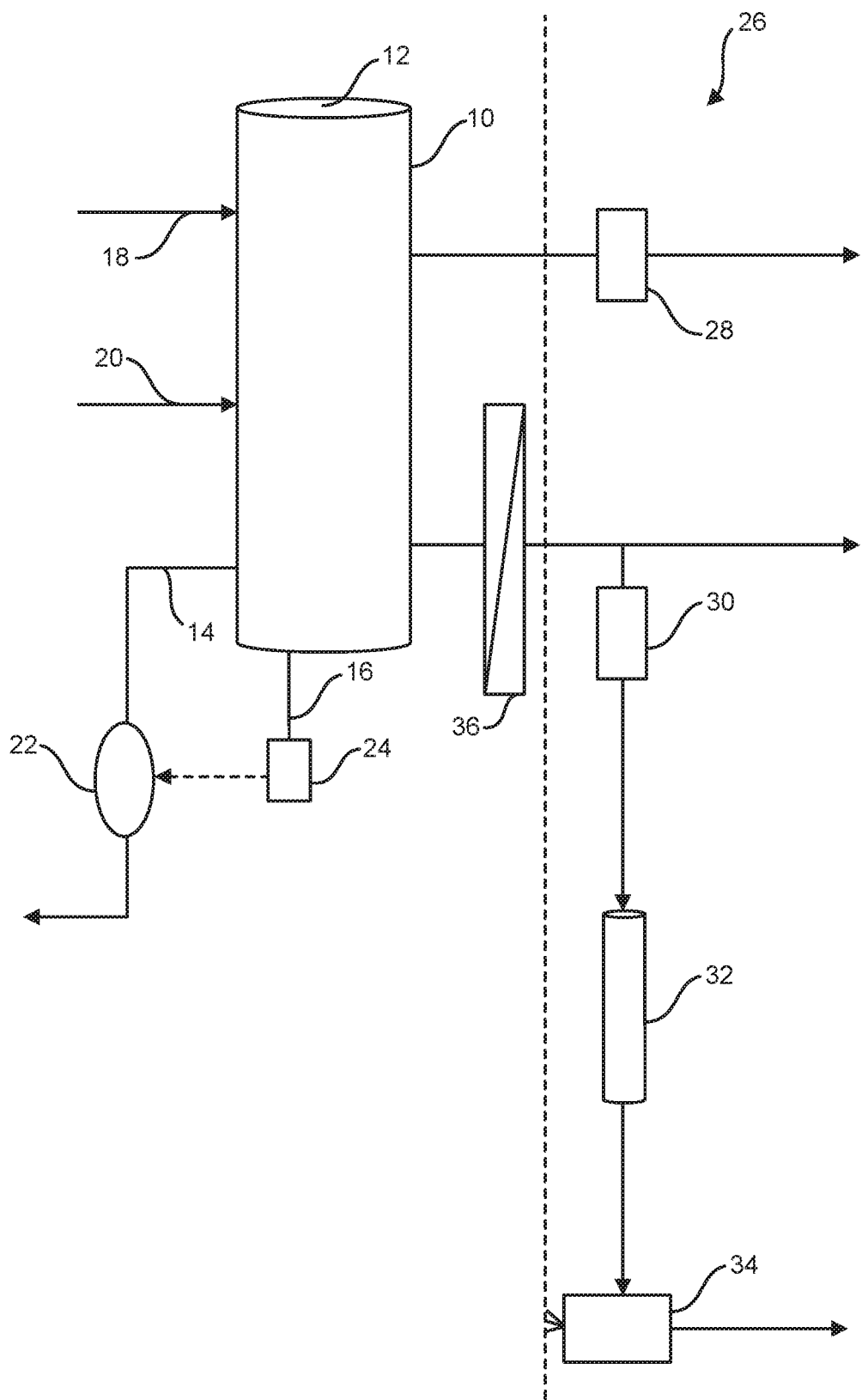
FIG. 1 is one embodiment of a perfusion bioreactor system in accordance with the present disclosure for creating and generating reference data regarding one or more quality attributes.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to a process and system for producing a bioproduct. For example, the process or system of the present disclosure can be incorporated into a cell culture process that uses open loop or closed loop control for monitoring one or more quality attributes, such as one or more parameters in a bioreactor containing the cell culture, and then automatically changing or varying the flow of an attribute influencing parameter in order to improve the quality and/or amount of cells produced.

The method and system of the present disclosure can be applied to any suitable cell culture product. For instance, the method of the present disclosure is particularly well suited to the production of biopharmaceuticals such as bio-therapeutic proteins. Bio-therapeutic proteins, for instance, are produced from genetically modified mammalian cells. In one embodiment, the cell cultures can be produced via recombinant gene expression in cell hosts. Such production can be from cell lines from established cultures, such as, for example, CHO, NSO, or PER.C6. These cells can express the protein of interest and subsequently secrete the protein into the media. It should be understood, however, that the process and techniques of the present disclosure are not limited to the production of proteins and that any suitable cell culture can be subjected to the controls described herein.

In producing cell cultures, one goal is to lower product variability and increase product quality by increasing control of quality attributes within the cell culture. The quality attributes can be maintained within predefined ranges by manipulating attribute influencing parameters. Attribute influencing parameters are typically defined experimentally in the cell culture process by systematically manipulating recipe variables, such as media components and other culture conditions, and observing the ultimate outcome in the propagating cell culture.

In the past, in order to control attribute influencing parameters so as to maintain quality attributes within preset limits, cell culture processes were propagated according to a predefined, tightly controlled recipe. The recipe was determined from laboratory scale experiments in order to produce cell cultures with a low degree of variation. Currently, greater emphasis is being placed on developing more aggressive open loop or closed loop control strategies where attribute influencing parameters are actively manipulated during the process within a defined range to achieve desired quality attribute properties. Unfortunately, however, successful application of quality attribute control requires constructing a control strategy that is labor intensive and time-consuming. For example, process optimization is typically carried out through many manually executed experiments followed by evaluation by those skilled in the art to understand the implications for process and media optimization. This approach takes a considerable amount of time and effort and often produces data that is not ideal for developing a product attribute quality control scheme.

In this regard, the present disclosure is directed to a method and system for efficiently relating attribute influencing parameters to quality attributes in cell cultures in order to develop reference data for use in generating predictive models employed by model predictive controllers for automating the growth of cell cultures. According to the present disclosure, a cell culture is grown in a pseudo-steady-state perfusion bioreactor and subjected to changes in attribute influencing parameters, such as a concentration of various feed components, in order to determine, monitor and record changes in quality attributes over time.

Use of a perfusion bioreactor in order to generate reference data relating to quality attributes can provide various advantages and benefits. The pseudo-steady-state perfusion bioreactor, for instance, allows independent manipulation of attribute influencing parameters, such as concentrations of media components, in a fashion that is more independent of the highly multivariate nature of cell culture processes. Thus, the use of a perfusion bioreactor can greatly simplify the detection of the effect of changing an attribute influencing parameter on a quality attribute. The pseudo-steady-state bioreactor also allows multiple manipulations of attribute influencing parameters to be carried out in sequence or simultaneously, without having to complete an entire batch process to detect the ultimate effect of the changes of the parameters on one or more quality attributes. Additionally, due to the fact that the perfusion bioreactor is at pseudo-steady-state, non-linearities, time-variants, and hysteresis effects can be detected by varying the order of the manipulations of the parameters and looking for changes in outcome of the quality attributes over time.

In order to generate reference data in accordance with the present disclosure, one or more attribute influencing parameters can be changed within the perfusion bioreactor in a controlled manner. These changes can be used to record and obtain data on at least one quality attribute. Of particular advantage, multiple quality attributes can be monitored simultaneously within the perfusion bioreactor. For instance, in one embodiment, a single attribute influencing parameter can be changed over time which may impact multiple quality attributes that are also measured and recorded. Alternatively, two or more attribute influencing parameters can be changed over time in order to monitor the effects on multiple quality attributes in parallel. Thus, the perfusion bioreactor system of the present disclosure can obtain meaningful reference data for use in predictive models for more than one quality attribute simultaneously as the cell culture within the bioreactor reacts to changes in one or more parameters.

The quality attribute monitored and controlled in accordance with the present disclosure can vary depending upon the particular application and the desired result. For instance, quality attributes that can be controlled include protein titer, lactate concentration, cell growth rate, and/or glycan composition. Glycan composition can include a degree of galactosylation, high mannose species, sialation and/or fucosylation. The quality attribute can also be glycan site occupancy. In another embodiment, the quality attribute being controlled may comprise a charge variant. For instance, the charge variant may relate to C-terminal lysine cleavage, deamidation, adduct formation, succinide formation, oxidation, C-terminal proline amidation, isomerization, and/or sialation. Still other quality attributes that can be controlled include aggregate concentration, clipping, disulfide oxidation, and a disulfide shuffling variant. Further quality attributes that can be monitored and controlled include fragmentation, disulfide shuffling, disulfide reduction, methionine oxidation, lysine variants, bispecific monoclonal antibody heterology, sequence variants and/or uncoded amino acid substitutions. The quality attribute can also be a process quality indicator such as ammonia concentration, viable cell density, cell size, cell viability, alanine concentration, and/or glutamine concentration.

Referring to FIG. 1, one embodiment of a perfusion bioreactor system that may be used in accordance with the present disclosure for generating reference data for a predictive model is illustrated. The diagram illustrated in FIG. 1 is for exemplary purposes only and in no way limits the type of perfusion bioreactor system that may be used to generate quality attribute information. In general, the perfusion bioreactor system can be configured to be a highly automated process development platform where short, parallel cell culture experiments can be carried out. Using the perfusion bioreactor system, reliable information regarding various quality attributes can be obtained in very short experimentation times using actively defined and controlled product quality attributes. As described above, in one embodiment, the perfusion bioreactor system can simultaneously produce reference data and other information for multiple quality attributes in parallel.

As shown in FIG. 1, the perfusion bioreactor system includes a perfusion bioreactor 10. The perfusion bioreactor 10 may comprise any suitable bioreactor depending upon the cell culture being propagated. For instance, the perfusion bioreactor 10 may comprise a fermenter, a stirred-tank reactor, a wave-type bioreactor, or the like. The perfusion bioreactor 10 in the embodiment illustrated in FIG. 1 comprises a hollow vessel or container that includes a bioreactor volume 12 for receiving a cell culture within a fluid growth medium. Not shown, the perfusion bioreactor 10 can be placed in association with a rotatable shaft coupled to an agitator for stirring the cell culture contained within the bioreactor volume 12.

The perfusion bioreactor 10 can be made from various materials. For instance, the bioreactor 10 can be made from a metal, such as stainless steel, and can be designed to be reused. Alternatively, the perfusion bioreactor 10 may comprise a single use bioreactor made from a rigid polymer or a flexible polymer film. When made from a rigid polymer, for instance, the bioreactor walls can be free standing. Alternatively, the bioreactor 10 can be made from a flexible polymer film or shape conforming material that can be liquid impermeable and can have an interior hydrophilic surface. In one embodiment, the perfusion bioreactor 10 can be made from a flexible polymer film that is designed to be inserted into a rigid structure, such as a metal container for assuming a desired shape.

The perfusion bioreactor 10 can have any suitable volume. For instance, the volume of the perfusion bioreactor 10 can be generally greater than about 50 ml, such as greater than about 500 ml. The volume of the perfusion bioreactor 10 is generally less than about 10 L, such as less than about 8 L, such as less than about 6 L, such as less than about 4 L, such as less than about 2 L.

The perfusion bioreactor 10 can also include various over components and equipment, such as baffles, spargers, gas supplies, heat exchangers, and the like which allow for the cultivation and propagation of biological cells.

The perfusion bioreactor 10 is designed so as to continuously receive various inputs, such as a nutrient media, and to continuously remove spent media so as to maintain pseudo-steady-state conditions within the cell culture contained within the bioreactor 10. For example, in one embodiment, the perfusion bioreactor 10 is operated so as to maintain a relatively constant volume of cell culture and media. For example, the perfusion bioreactor 10 can be operated so that the volume within the bioreactor does not vary by more than 10%, such as by no more than about 8%, such as by no more than about 5%, such as by no more than about 3%.

There are various different ways in order to remove spent media from the perfusion bioreactor 10 without depleting the biological cells. For instance, in one embodiment, the perfusion bioreactor can include attachment devices, such as capillary fibers or membranes, which the cells bind to for preventing their release. In other embodiments, the perfusion bioreactor 10 can include a filtration system that maintains a desired cell density with the bioreactor. By continuously removing spent media from the perfusion bioreactor 10 and replacing it with new media, nutrient levels can be controlled and maintained for varying the growing conditions within the bioreactor. In addition, cell waste can be removed in a controlled fashion to avoid toxicity.

The perfusion bioreactor 10 can include a plurality of ports. The ports can allow supply lines and feed lines into and out of the bioreactor 10 for adding and removing fluids and other materials. In addition, the one or more ports may be for connecting to one or more probes for monitoring conditions within the perfusion bioreactor 10. In addition, the perfusion bioreactor 10 can be placed in association with a load cell for measuring the mass of the culture within the bioreactor.

In the embodiment illustrated in FIG. 1, for instance, the perfusion bioreactor 10 includes effluent ports 14 and 16 and a plurality of influent ports 18 and 20. The effluent port 14 is for continuously or periodically removing media and biomass from the perfusion bioreactor 10. The effluent port 14 can be in fluid communication with a pump 22 for controlling flow rates. In one embodiment, the system can further include a biomass sensor 24 that can be placed in communication with the pump 22. The biomass sensor 24, for instance, can be a capacitance probe. The biomass sensor 24 can be used to assay biomass concentrations within a sample of cell culture obtained from the perfusion bioreactor 10 via port 16. Based upon information received from the biomass sensor 24, nutrient media flow rates into the perfusion bioreactor 10 and/or effluent flow rate out through the ports 14 can be controlled or automatically adjusted based on the determined cell concentration in order to maintain the cell concentration within preset limits. For example, in one embodiment, the biomass sensor 24 can determine biomass concentrations using a probe and can send the information to a controller. The controller can then be used to control the amount of media being withdrawn from the perfusion bioreactor 10 by the pump 22 and/or can also control the amount of nutrient media being fed to the bioreactor 10.

As shown in FIG. 1, the perfusion bioreactor 10 can include a plurality of influent ports such as ports 18 and 20. The influent ports 18 and 20, for instance, can be used to not only feed or supply a nutrient media to the perfusion bioreactor 10 but can also be used to vary one or more attribute influencing parameters in accordance with the present disclosure. For instance, in one embodiment, port 18 can be used to feed a nutrient media into the perfusion bioreactor 10. As used herein, a nutrient media or nutrient refers to any fluid, compound, molecule, or substance that can increase the mass of a bioproduct, such as anything that may be used by an organism to live, grow or otherwise add biomass. For example, a nutrient feed can include a gas, such as oxygen or carbon dioxide that is used for respiration or any type of metabolism. Other nutrient media can include carbohydrate sources. Carbohydrate sources include complex sugars and simple sugars, such as glucose, maltose, fructose, galactose, and mixtures thereof. A nutrient media can also include an amino acid. The amino acid may comprise, glycine, alanine, valine, leucine, isoleucine, methionine, proline, phenylalanine, tryptophan, serine, threonine, asparagine, glutamine, tyrosine, cysteine, lysine, arginine, histidine, aspartic acid and glutamic acid, single stereoisomers thereof, and racemic mixtures thereof. The term "amino acid" can also refer to the known non-standard amino acids, e.g., 4-hydroxyproline, ε-N,N,N-trimethyllysine, 3-methylhistidine, 5-hydroxylysine, O-phosphoserine, γ-carboxyglutamate, γ-N-acetyllysine, ω-N-methylarginine, N-acetylserine, N,N,N-trimethylalanine, N-formylmethionine, γ-aminobutyric acid, histamine, dopamine, thyroxine, citrulline, ornithine, β-cyanoalanine, homocysteine, azaserine, and S-adenosylmethionine. In some embodiments, the amino acid is glutamate, glutamine, lysine, tyrosine or valine.

The nutrient media can also contain one or more vitamins. Vitamins that may be contained in the nutrient media include group B vitamins, such as B12. Other vitamins include vitamin A, vitamin E, riboflavin, thiamine, biotin, and mixtures thereof. The nutrient media can also contain one or more fatty acids and one or more lipids. For example, a nutrient media feed may include cholesterol, steroids, and mixtures thereof. A nutrient media may also supply proteins and peptides to the bioreactor. Proteins and peptides include, for instance; albumin, transferrin, fibronectin, fetuin, and mixtures thereof. A growth medium within the present disclosure may also include growth factors and growth inhibitors, trace elements, inorganic salts, hydrolysates, and mixtures thereof, Trace elements that may be included in the growth medium include trace metals. Examples of trace metals include cobalt, nickel, and the like.

In the embodiment illustrated FIG. 1, only two ports 18 and 20 are shown for feeding materials to the perfusion bioreactor 10. It should be understood, however, that the perfusion bioreactor 10 may include may include more than two media feeds. In this manner, various different attribute influencing parameters can be isolated and fed to the perfusion bioreactor 10 for controlling, changing and/or varying the amount of attribute influencing parameter contained in the bioreactor.

In addition to ports 14, 16, 18 and 20, the perfusion bioreactor 10 can include various other ports for adding materials to the bioreactor, removing materials from the bioreactor or testing various conditions within the bioreactor. For instance, in one embodiment, the perfusion bioreactor 10 can include feed gas ports in order to feed gases such as carbon dioxide and/or oxygen into the bioreactor 10. In addition, the perfusion bioreactor 10 can include a pH sensor, a dissolved oxygen sensor, or various other monitoring and control components. pH and dissolved oxygen, for instance, can be measured inline and can be continuously or periodically monitored as one or more attribute influencing parameters within the bioreactor are changed or varied.

In addition, as shown in FIG. 1, the bioreactor system may further include a sampling and testing system 26. In one embodiment, for instance, the perfusion bioreactor system may be automated to allow for increased data generation. For instance, cell containing samples and cell free samples can be automatically sampled using an aseptic auto sampler to deliver samples to a liquid handling robot that automates the sample preparation. It should be understood, however, that in other embodiments, human sampling can also be used.

As shown in FIG. 1, the sampling and testing system 26 can be used to measure a plurality of parameters during propagation of a cell culture within the perfusion bioreactor 10. The sampling and testing system 26, for instance, can measure and monitor not only attribute influencing parameters within the bioreactor 10, but also one or more quality attributes. The attribute influencing parameters and/or the quality attributes can be tested and monitored simultaneously. For instance, in one embodiment, one or more attribute influencing parameters can be controlled by the process or system of the present disclosure and measured in conjunction with one or more quality attributes to determine the influence that the attribute influencing parameters have on the quality attributes.

As shown in FIG. 1, the sampling and testing system 26 can include a cell containing sampling device 28. Samples obtained from the sampling device 28, for instance, can be sent to an analyzer for at line or off line analysis of the cell culture. Any suitable analyzer can be used in order to determine, measure and monitor one or more parameters and/or quality attributes. For instance, one suitable instrument is the Nova FLEX Bioprofile 400 Analyzer sold by Nova Biomedical. The above analyzer is capable of measuring multiple parameters in a single sample.

The perfusion bioreactor system as shown in FIG. 1 further includes a cell free sampling device 30. As shown in FIG. 1, the cell free sampling device 30 is positioned downstream from a cell retention device 36. The cell retention device 36 filters cells from a sample being obtained from the perfusion bioreactor 10, and allows removal of cell culture media from the bioreactor without removing biomass for perfusion level and biomass controllers. One suitable cell retention device is the ATF2 system sold by Refine.

Cell free samples obtained from the sampling device 30 can be analyzed for various different parameters and quality attributes. For instance, a cell free permeate can be analyzed for various components. In addition, in one embodiment, the sampling and testing system 26 can also be used to analyze protein content in a sample. For instance, a cell free sample obtained from the cell free sampling device 30 can be fed to a protein column 32. One suitable protein separation column is the mAb Select protein-A column sold by GE. Samples obtained from the protein column 32 can then be transferred to a chilled sample rack 34 for protein quality analysis.

In accordance with the present disclosure, the perfusion bioreactor system as shown in FIG. 1 can be used to rapidly collect reference data for use in predictive models regarding a plurality of quality attributes. Information regarding a plurality of quality attributes can be obtained simultaneously and in parallel. This information is obtained and collected by controlling and varying one or more attribute influencing parameters within the perfusion bioreactor 10. Attribute influencing parameters that can be manipulated in accordance with the present disclosure in order to influence one or more quality attributes include any suitable nutrient, sugar, amino acid, lipid, vitamin, metal salt, or the like. The quality attribute can include glutamate concentration, glucose concentration, asparagine concentration, temperature, nutrient feed rate, pH, galactose concentration, trace metals, carbohydrates, mannose concentration, N-acetyl mannosamine concentration, sucrose concentration, lysine concentration, methionine concentration, serine concentration, dissolved oxygen, applied shear rate, manganese concentration, copper concentration, iron concentration, selenium concentration, and the like. In general, the attribute influencing parameters manipulated in accordance with the present disclosure can be any attribute influencing parameter that can have an effect on one or more quality attributes.

Each attribute influencing parameter is varied in the perfusion bioreactor 10 over time. The manner in which the attribute influencing parameter is changed or varied depends upon various factors. In general, the change in the attribute influencing parameter is in magnitude. For instance, if the attribute influencing parameter is a component within the nutrient media or fed separately to the perfusion bioreactor 10, the attribute influencing parameter is changed by varying the feed rate of the parameter to the reactor. If the attribute influencing parameter is pH, on the other hand, the change can be a change in pH by adding or removing from the perfusion bioreactor 10 a suitable acid or base.

Each attribute influencing parameter that is changed and manipulated within the perfusion bioreactor 10 can vary depending upon various factors and the quality attribute being monitored. In general, each attribute influencing parameter can be changed and varied within the reactor according to any suitable recipe that will provide reliable information regarding one or more quality attributes. For example, in one embodiment, the magnitude of each attribute influencing parameter being manipulated in the perfusion bioreactor 10 can vary from a minimum magnitude to a maximum magnitude. Alternatively, the magnitude of the attribute influencing parameter can vary in more of a random fashion changing between lower magnitudes and higher magnitudes over time.

Figure 3:
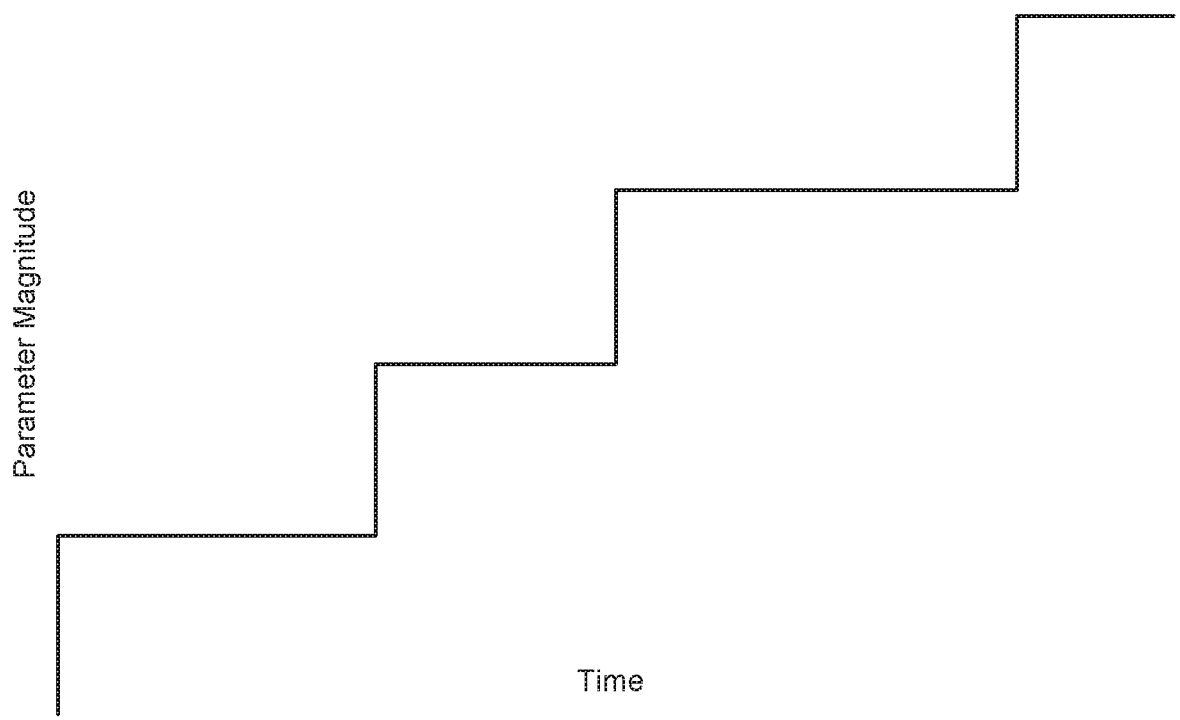
FIG. 3 is one embodiment of a graph illustrating changes in an attribute influencing parameter over time in a perfusion bioreactor.

In one embodiment, one or more attribute influencing parameters are varied within the perfusion bioreactor 10 in a stepwise manner. For instance, referring to FIG. 3, in one embodiment, an attribute influencing parameter can be fed to the perfusion bioreactor 10 in a stepwise manner such that the magnitude of concentration of the parameter within the bioreactor remains constant for a certain period of time and then is increased to a new level, maintained constant for a defined period of time and then raised again to a new level. In the embodiment illustrated in FIG. 3, the magnitude of concentration of the parameter is constantly raised in a stepwise manner from a minimum to a maximum. While the attribute influencing parameter is being manipulated, at least one and preferably a plurality of quality attributes are being measured and determined from the cell culture within the perfusion bioreactor 10. In one embodiment, after each stepwise change in the attribute influencing parameter, the one or more quality attributes are monitored over time until steady state within the cell culture is obtained. In an alternative embodiment, however, further stepwise changes are made in the attribute influencing parameter before steady state in the cell culture is achieved. For instance, by making stepwise changes before reaching steady state, more information about one or more quality attributes can be obtained in a shorter period of time. In addition, for many embodiments, the useful data with respect to one or more quality attributes is based upon the gradient of the attribute influencing parameter and its effect on the cell culture and not with the cell culture reaching steady state based upon the stepwise change.

Figure 4:
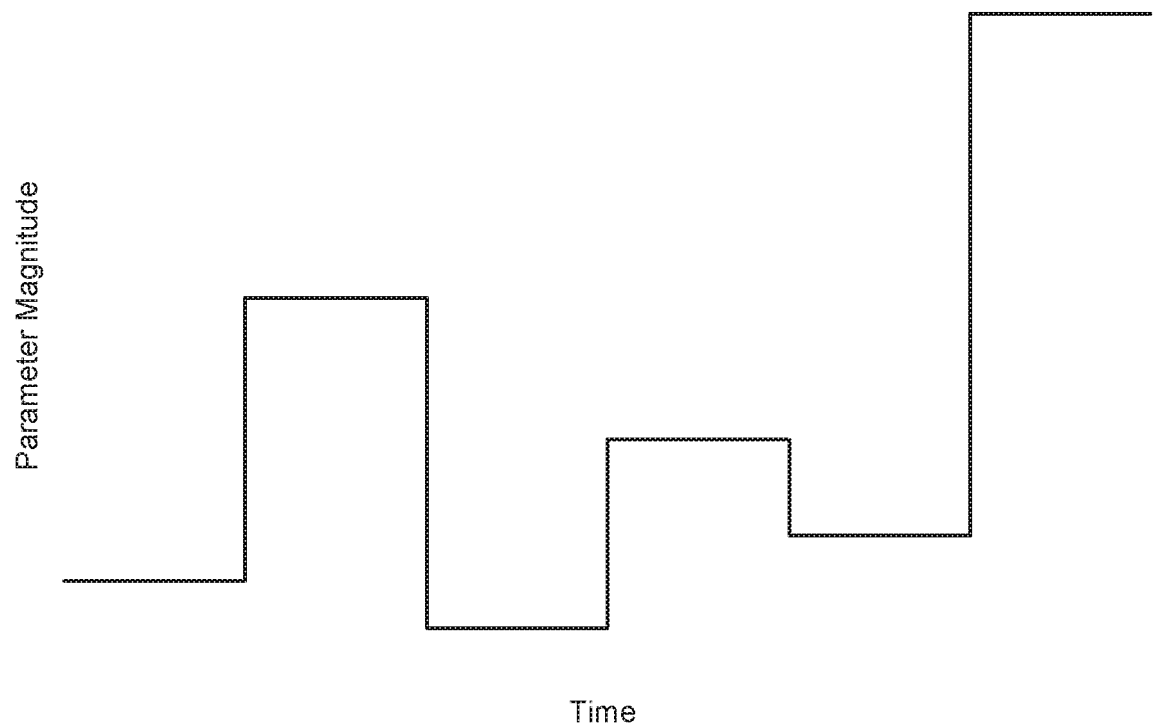
FIG. 4 is another embodiment of a graph illustrating changes in an attribute influencing parameter over time in a perfusion bioreactor.

Referring to FIG. 4, another embodiment of a manner in which an attribute influencing parameter can be varied within the perfusion bioreactor 10 is illustrated. As shown in FIG. 4, the magnitude or concentration of the attribute influencing parameter is changed or varied in a stepwise manner. Instead of going from a minimum value to a maximum value, however, the magnitude or concentration of the attribute influencing parameter is changed in more of a random manner. In particular, the magnitude or concentration of the attribute influencing parameter oscillates between lower values and higher values. Having the stepwise changes occur in a random manner, in some embodiments, provides better information about one or more quality attributes that are being monitored during the stepwise changes.

Figure 5:
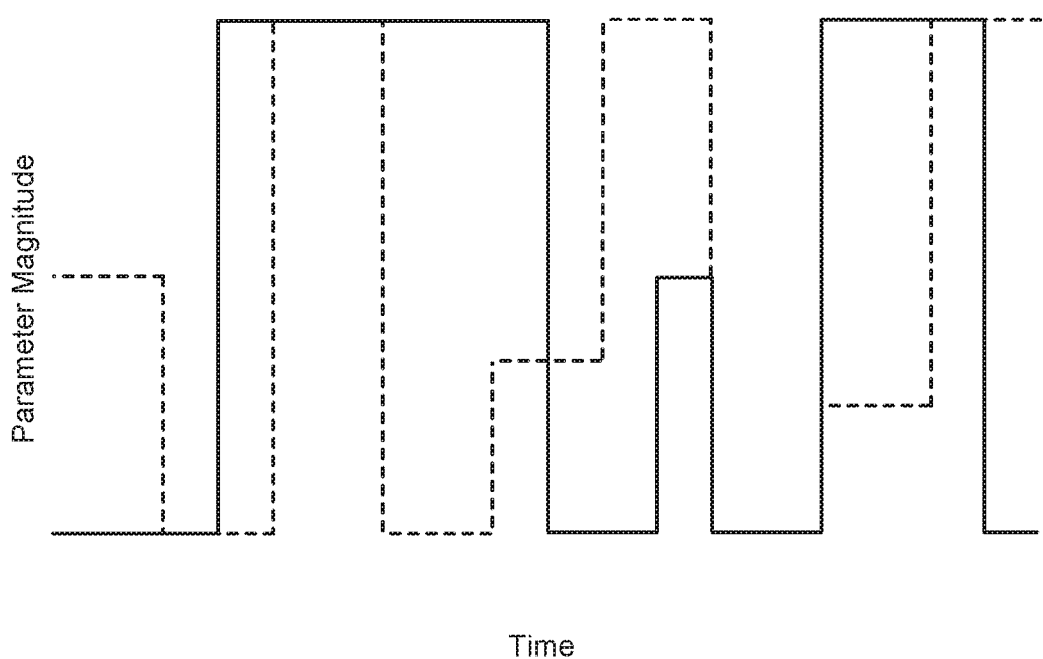
FIG. 5 is one embodiment of a graph illustrating changes in more than one attribute influencing parameter over time in a perfusion bioreactor in accordance with the present disclosure.

In accordance with the present disclosure, more than one attribute influencing parameter can be manipulated and changed within the perfusion bioreactor 10 simultaneously. For instance, referring to FIG. 5, two concentration or magnitude profiles are shown for two different attribute influencing parameters over time being fed to the perfusion bioreactor 10. As shown, the concentration of each attribute influencing parameter can be changed and controlled simultaneously, but independently of each other. For example, as shown in FIG. 5, each attribute influencing parameter is changed according to a different stepwise recipe in a random manner. Multiple attribute influencing parameters can be manipulated and changed over time simultaneously while monitoring and obtaining useful reference data regarding one or more quality attributes.

While the attribute influencing parameters are being manipulated and measurements are being taken regarding one or more quality attributes, the perfusion bioreactor 10 can operate at pseudo-steady-state. Operating the perfusion bioreactor 10 at steady-state conditions allows for independent manipulation of the attribute influencing parameters in a fashion that is more independent of the highly multivariate nature of the cell culture process, allowing for data generation of multiple quality attributes independently and in parallel. For example, the perfusion bioreactor 10 can be operated such that the cell density of the cell culture remains relatively constant. For instance, the cell density can be maintained in a state that mirrors an intermediate stage of the cell culture during a cell culture batch process. For example, in one embodiment, the cell density and the conditions within the bioreactor can be maintained at conditions that are similar to about day 4 to about day 10, such as from about day 5 to about day 8 of a batch process. In an alternative embodiment, the perfusion bioreactor can be operated at a relatively high cell density.

In one embodiment, the cell density can vary by no more than about 20% (±20%), such as vary by no more than about 15%, such as vary by no more than about 10%, such as vary by no more than about 5% during the process. In one particular embodiment, for instance, the cell density can be maintained at generally greater than about 500,000 cells/mL, such as greater than about 800,000 cells/mL, such as greater than about 1,000,000 cells/mL, such as greater than about 10,000,000 cells/m L, such as greater than about 50,000,000 cells/mL, such as greater than about 80,000,000 cells/mL and generally less than about 200,000,000 cells/mL, such as less than about 150,000,000 cells/mL, such as less than about 100,000,000 cells/mL, such as less than about 50,000,000 cells/mL, such as less than about 30,000,000 cells/mL. It should be understood, however, that the cell density can vary widely and is dependent upon the type of cells being propagated within the bioreactor. The above ranges for instance, are particularly well suited when processing the mammalian cells.

In addition to maintaining a relatively constant cell density, the perfusion bioreactor 10 can also be operated so as to maintain a relatively constant volume. For instance, the volume can vary by no more than about 20%, such as by no more than about 15%, such as by no more than about 10%, such as by no more than about 5%, such as by no more than about 2% during the process. In one embodiment, the nutrient feed rate can be held at a constant rate and the cell-free permeate and the effluent 14 and/or pump 22 can be manipulated to hold reactor volume constant. In one embodiment, for instance, a controller can maintain a relatively constant volume within the bioreactor by measuring vessel weight and manipulating the pump rate to achieve a particular setpoint. Simultaneously, the controller or a different controller can control the cell density based upon capacitance values obtained from the biomass sensor 24 and then manipulating the pump rate to maintain the cell density within preset ranges.

Of particular advantage, the system and process of the present disclosure for obtaining meaningful quality attribute data can occur very efficiently and in a relatively short amount of time. For instance, the attribute influencing parameters can be manipulated and information regarding one or more quality attributes can be obtained in a period of time of less than about 4 days, such as less than about 3 days, such as less than about 48 hours, such as even in an amount of time less than about 30 hours. Data is generated in an amount of time of at least about 12 hours, such as at least about 24 hours.

As described above, during the process, one or more quality attributes are monitored and measured. In one embodiment, for instance, at least two, such as at least three, such as at least four quality attributes are monitored and measured in parallel during the process. For instance, from about two to about eight, such as from about two to about six quality attributes can be measured simultaneously. The measurements can be continuously or periodically while the attribute influencing parameters are varied. Information obtained regarding the quality attributes can then be used as reference data in a predictive model for controlling conditions within a commercial bioreactor process, such as in a batch process.

Many different quality attributes can be monitored and measured during the process. Examples of quality attributes that can be monitored include, for instance, lactate concentration, protein amount or concentration, glycan composition, a charge variant, an aggregate, disulfide oxidation, a disulfide shuffling variant, and the like.

The reference data produced according to the process of the present disclosure can be used in any suitable predictive model. In one embodiment, the data can be fed into machine learning tools that can identify patterns in the data for optimizing feed rates or other process conditions during the propagation of a cell culture. Ultimately, the reference data can be used to improve the predictability of cell culture processes for producing cell cultures with improved properties and increased titer.

Figure 2:
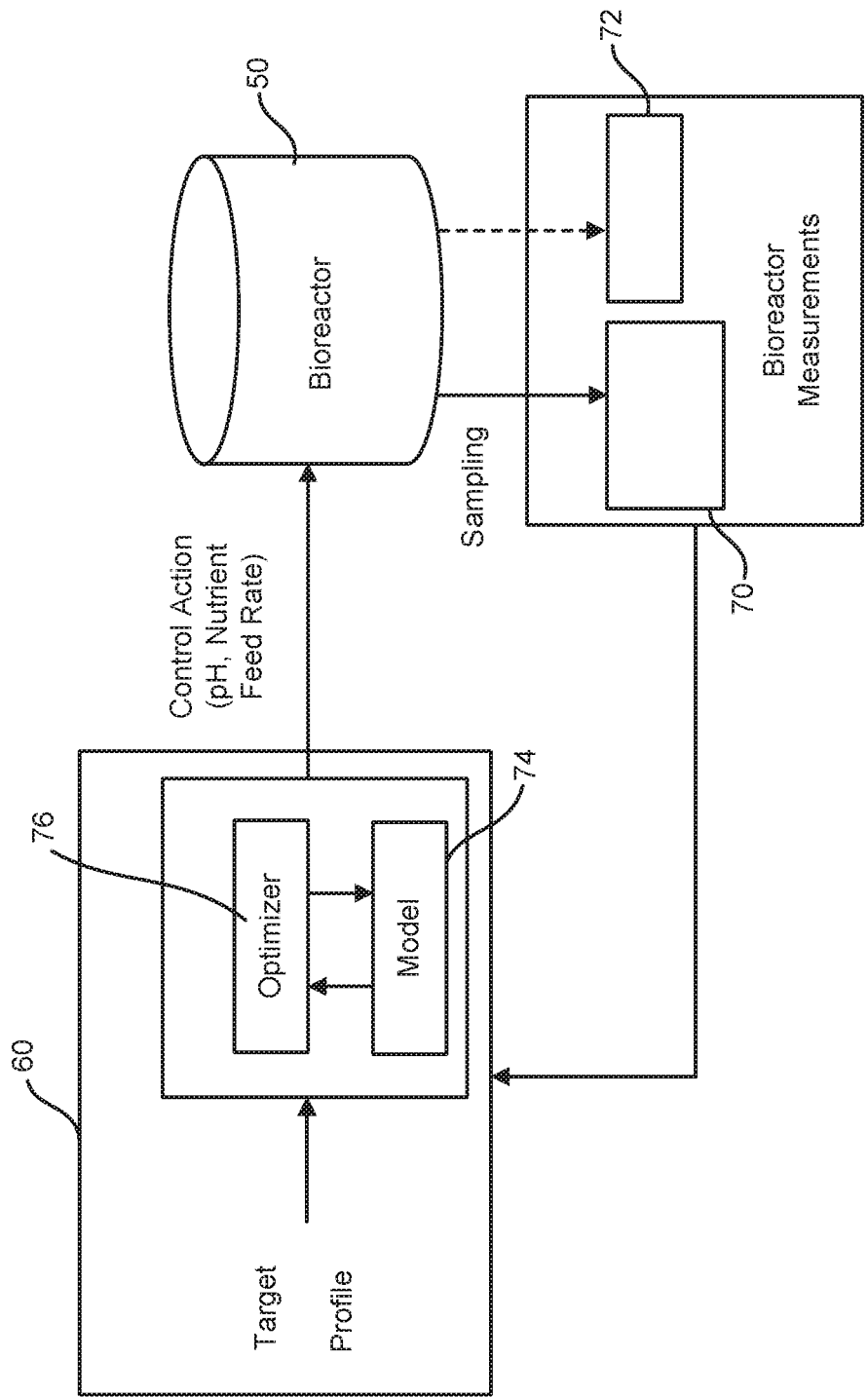
FIG. 2 is one embodiment of cell culture process and system that may use reference data generated in accordance with the present disclosure.

Referring to FIG. 2, one embodiment of a bioreactor system in accordance with the present disclosure that may use the reference data obtained in the process of FIG. 1 is shown. As shown, a cell culture is cultivated in the bioreactor 50 for an incubation period and then harvested. During the incubation, various parameters in the bioreactor 50 are monitored. The parameters are measured by one or more analyzers 70. The analyzer 70 periodically or continuously monitors various parameters and/or quality attributes which are communicated to the controller 60.

The controller can include a control model that, based upon inputted data, is capable of forecasting quality attribute concentrations in the future as the cell culture continues to propagate. In one embodiment, for instance, the controller can provide an early warning system that produces a percent probability as to whether the cell culture in the bioreactor 10 is within preset limits. The controller can also include a predictive model that accurately predicts future quality attribute concentrations. For instance, in one embodiment, the controller 60 can forecast quality attribute concentration trajectories that predict concentrations through the entire incubation period until a cell culture is harvested. In one embodiment, the controller 60 can also be configured to suggest or automatically implement corrective actions in case one or more quality attributes are outside preset limits. In accordance with the present disclosure, the controller contains reference data obtained from the process in FIG. 1 for calculating future quality attribute concentrations.

The controller 60 may comprise one or more programmable devices or microprocessors. The controller 60 can be in communication with one or more feeds and with one or more effluents. The controller can be in communication with various sensors and probes, such as a pH sensor, a dissolved oxygen sensor, and gas supplies that feed gas to the bioreactor 50. The controller 60 can be configured to increase or decrease the flow of materials into and out of the bioreactor 50 based upon calculated future concentrations of quality attributes. The controller 60 can operate in an open loop manner or in a closed loop manner.

As shown in FIG. 2, the controller 60 can be programmed with a target quality attribute profile. The controller 60 can include at least one control model 74. In one embodiment, for instance, the controller can include a classification model and a predictive model. The classification model can be configured to produce a percent probability that the incubation period of the cell culture will end within present limits. The classification model can use various multivariate methods including a partial least squares analysis alone or in combination with a linear discriminant analysis. The classification model may also use classification trees, support vector machines, and the like. In one embodiment, a median of the percent probabilities resulting from each classification model can be employed as the final percent probability for the cell culture. In one embodiment, the percent probability that the cell culture will end in a desired state can be presented to a user in order to allow the user to determining if intervention is required during the growth of the cell culture in order to ensure that the incubation period of the cell culture ends with desired quality attribute concentration limits.

The controller 60 can also include a predictive model. The predictive model can determine future quality attribute concentration trajectories over the entire incubation period. In addition, the predictive controller can be configured to predict how changes in one or more conditions within the bioreactor 50 over a specified control horizon will affect concentrations over a specified prediction horizon. For example, as shown in FIG. 2, the predictive model 74 can be in communication with an optimizer 76. The optimizer 76 can be configured to simulate results within the bioreactor 10 if one or more conditions are varied. The conditions can include changing nutrient media feed rate and thereby changing glucose concentration, glutamate concentration, asparagine concentration, and the like. In addition to nutrient feed rates, the optimizer 76 can also change various other conditions including pH and gas rate additions. The optimizer 76 can run multiple simulations and numerous iterations in order to determine if corrective action is needed within the cell culture, and, if so, not only the best conditions to change in the bioreactor but the magnitude of the change. The predictive model ultimately determines variations in manipulated variables in order to minimize future deviations of the concentrations from a specified referenced trajectory. For example, the controller can employ the predictive model in the optimizer to determine the optimal variations in the input parameters that minimize future deviations of the output(s) from specified reference trajectories. As future data is fed to the controller 60, the optimizer 76 can continue to run simulations over the entire incubation period in order to further change or tweak manipulated variables thereby changing one or more conditions within the cell culture.

The reference data produced from the process of the present disclosure can dramatically improve operation of the classification model and the predictive model. For example, the reference data can include quality attribute concentration trajectories in cell cultures as one or more attribute influencing parameters are varied. This information can greatly improve the predictability of the controller 60.

The predictive model can run simulations and make determinations based on using various multivariate methods. In one embodiment, for instance, the concentration trajectories can be determined by minimizing or optimizing the variations of the attribute influencing parameters in the predictive model in order to minimize weighted squared deviations of quality attribute concentration predictions from prescribed reference trajectories and weighted squared deviations and changes in each of the manipulated variables. This optimization can be performed subject to linear inequality constraints depending upon the amount of each manipulated variable can change over time.

In one embodiment, the predictive model can include a predictive control algorithm that employs reduced-order linear models such as a reduced order time varying autoregressive exogenous model (ARX model). Techniques that may be used in the predictive model include a neural network, support vector machines, latent variable modeling including partial least squares analysis. In addition, decision trees and linear discriminant analysis can be used.

In one embodiment, at least two multivariate methods are incorporated into the predictive model. For instance, the predictive model can include at least two of the neural network model, support vector machines, and latent variant modeling in determining concentration predictions.

In one embodiment, the predictive model is a nonlinear ARX model that includes model regressors and a nonlinearity estimator. The nonlinearity estimator can include both linear and nonlinear functions that act on the model regressors to give the model output.

In order to control quality attribute concentrations in the future, one or more conditions within the bioreactor can be changed. For example, one or more attribute influencing parameters within the bioreactor can be selectively controlled in order to control quality attribute concentrations. The condition being changed can include pH, carbohydrate concentrations such as glucose concentration, amino acid concentration, such as glutamate concentration and/or asparagine concentration, or the like. The pH of the cell culture can be changed by adding an acid or base to the cell culture, such as feeding carbon dioxide gas through the sparger and/or adding sodium bicarbonate to the cell culture. Carbohydrate concentration and/or amino acid concentration within the cell culture can be changed and modified by changing the nutrient media fed being feed to the bioreactor 50.

Of particular advantage, the controller 60 can also include a robust predictive model that can not only be scalable for different bioreactor types and bioreactor volumes, but can also be effective against multiple and diverse cell lines. For instance, the predictive model uses more than one multivariate technique, such as when using two multivariate techniques or three multivariate techniques making the model well suited for use across multiple cell lines.

In addition to monitoring one or more attribute influencing parameters, the controller can control various other process conditions. For instance, the controller can be in communication and control thermocirculators, load cells, control pumps, and receive information from various sensors and probes. For instance, the controller may control and/or monitor the oxygen tension, the temperature, the agitation conditions, the pressure, foam levels, and the like. For example, the controller can receive temperature information and control fluids being feed to a water jacket surrounding the bioreactor for increasing or decreasing temperature.

Through the process of the present disclosure, cell cultures can be grown with excellent product characteristics. For instance, cell cultures can be grown with excellent viability characteristics. For example, viability can be measured by dividing the viable cell count with the total cell count, which are two parameters that can both be measured during the process. Cell cultures can be grown in accordance with the present disclosure having a viability ratio as described above of greater than about 0.6, such as greater than about 0.7, such as greater than about 0.8, such as greater than about 0.9. In fact, the viability ratio can be greater than about 0.94, such as greater than about 0.96, such as greater than about 0.98.

Figure 6:
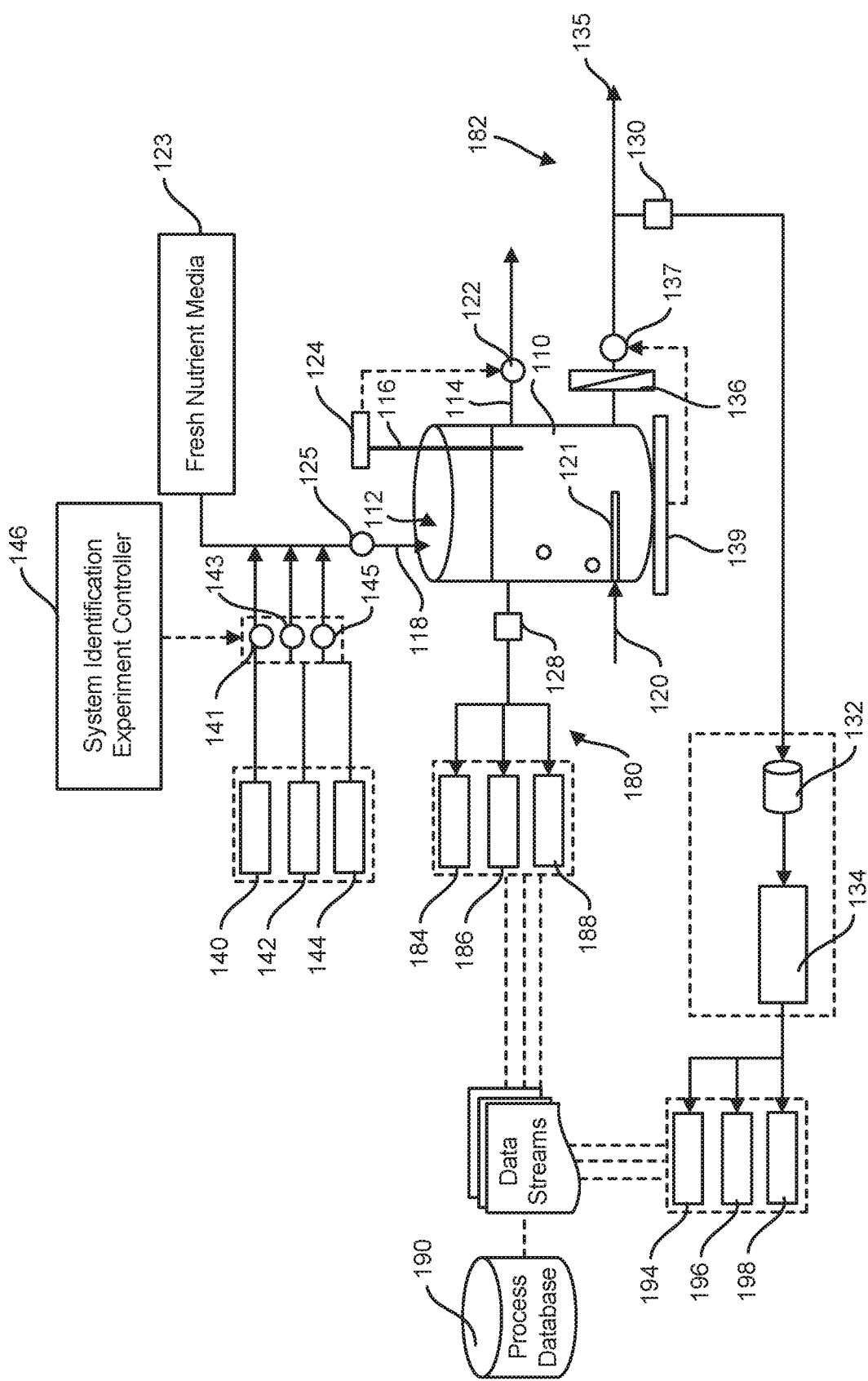
FIG. 6 is another embodiment of a perfusion bioreactor system in accordance with the present disclosure.

The system of the present disclosure for creating and generating reference data can have many different configurations and can be completely automated. Referring to FIG. 6, for instance, another embodiment of a perfusion bioreactor system capable of generating reference data for input into the model controller and optimizer in FIG. 2 is shown.

The system illustrated in FIG. 6 is similar to the system in FIG. 1 and includes a perfusion bioreactor 110. The perfusion bioreactor 110 can comprise a hollow vessel or container that includes a bioreactor volume 112 for receiving a cell culture within a fluid growth medium. The perfusion bioreactor 110 can include a plurality of ports. For instance, the system can include effluent ports 114 and 116. The effluent port 114 is for continuously or periodically removing media and biomass from the perfusion bioreactor 110. The effluent port 114 can be in fluid communication with a pumping device such as a cell bleed pump 122 for controlling flow rates. The system can further include a biomass sensor 124 which can be a capacitance probe. The biomass sensor 124 can be in fluid communication with the effluent 116. The biomass sensor 124 can be used to assay biomass concentration within the perfusion bioreactor 110.

The perfusion bioreactor 110 can also include a plurality of influent ports, such as ports 118 and 120. Influent ports 120, for instance, can be used to feed gases into the perfusion bioreactor 110. Gasses can include, for instance, oxygen, carbon dioxide, air, or mixtures thereof. The influent port 120 can be in communication with a sparger 121 that distributes the gases throughout the cell culture contained within the perfusion bioreactor 110.

The influent port 118, on the other hand, can be used to feed fluids, such as liquids, suspensions, emulsions, and the like into the perfusion bioreactor 110. For example, as shown, the influent port 118 is in fluid communication with a media supply 123 which can feed media to the perfusion bioreactor 110 using a pump 125.

In accordance with the present disclosure, the system illustrated in FIG. 6 further includes a plurality of attribute influencing parameter inputs or component inputs, such as component inputs 140, 142, and 144. Each component input 140, 142, and 144 is in communication with a corresponding flow control device 141, 143, and 145. The flow control devices 141, 143, and 145 can comprise pumps and/or valves. Each of the component inputs 140, 142 and 144 are in fluid communication with the influent port 118. In the embodiment illustrated, for instance, the components are blended with a nutrient media and fed to the perfusion bioreactor 110. In the embodiment illustrated in FIG. 6, the system includes three different attribute influencing parameter inputs or component inputs. It should be understood, however, that the system can include more component inputs as desired. For instance, the system can include from about two to about ten component inputs. The component inputs can also comprise other types of inputs in other embodiments. For instance, in an alternative embodiment, one of the component inputs can be a temperature regulator for the perfusion bioreactor 110.

In order to manipulate the attribute influencing parameters being fed to the perfusion bioreactor 110, the system can include an input controller 146. The input controller 146 can control the flow control devices 141, 143 and 145 for controlling and manipulating the quantity of the attribute influencing parameters being fed to the perfusion bioreactor 110. In one embodiment, for instance, the input controller 146 can be configured to feed to the perfusion bioreactor 110 a plurality of attribute influencing parameters from the component inputs 140, 142 and 144 according to a recipe that will influence quality attributes within the cell culture. In this manner, one or more quality attributes can be monitored and measured as the attribute influencing parameters are varied. A relationship can then be established between a quality attribute and one or more attribute influencing parameters.

As described above, in one embodiment, the input controller may only control a single attribute influencing parameter that may have an effect on multiple quality attributes. Alternatively, the input controller 146 may control a plurality of attribute influencing parameters that have an effect or influence a plurality of quality attributes. By carefully controlling the manner in which the attribute influencing parameters are varied using the input controller 146, correlations can be made between the attribute influencing parameters and the quality attributes for producing reference data that can be used in downstream cell culture systems.

In order to monitor and record quality attribute information, the system illustrated in FIG. 6 includes sample collection subsystems. For example, in the embodiment illustrated in FIG. 6, the system includes a first sample collection subsystem 180 and a second sample collecting subsystem 182. The sample collection subsystem 180 is for collecting and analyzing cell culture samples that contain cell matter or cell material. The sample collection subsystem 180 includes a cell containing sampling device 128 that can feed samples to analyzers 184, 186 and 188. In one embodiment, samples are automatically removed from the bioreactor and fed to the analyzers 184, 186 and 188. Any suitable analyzer can be used in order to determine, measure and monitor one or more quality attributes. At least one of the analyzers 184, 186 and 188 may comprise a Nova FLEX Bioprofile 400 Analyzer for analyzing quality attributes contained within or associated with cell matter. In one embodiment, the information created by the analyzers is fed through a data stream into a system database 190.

The sample collection subsystem 182, on the other hand, is for collecting samples from the bioreactor that are cell free. For instance, the system can include a cell retention device 136 placed in combination with a permeate pump 137. A reactor scale 139 can be in communication with the permeate pump 137 for maintaining steady state within the perfusion bioreactor 110 by maintaining the amount of cell culture contained within the bioreactor within preset limits.

As shown in FIG. 6, a cell free permeate is pumped from the perfusion bioreactor 110 and split into two streams. The first stream is a permeate eluent stream 135. The second stream, on the other hand, is analyzed for quality attributes. For instance, the permeate is fed to a cell free sampling device 130 which is positioned downstream from the cell retention device 136. As shown, from the cell free sampling device 130, the permeate is fed to a protein separation column 132 and to a sample prep device 134, which may, for instance, chill the sample for protein quality analysis. From the sample prep device 134, samples are fed to various different analyzers 194, 196 and 198 for analyzing for various different quality attributes. The analyzers 194, 196 and/or 198 may comprise, for instance, mass spectrometers, high performance liquid chromatographs, and the like. The analyzers 194, 196 and 198 can automatically transfer quality attribute information via a data stream into a system database 190. In one embodiment, the sample collection subsystem 182 is completely automated and periodically or continuously removes samples from the perfusion bioreactor 110, analyzes the samples and inputs the information into the database 190.

The system database 190 can be configured to store the collected reference data in a media configured to transfer the reference data to a controller. The controller can then use the reference data for controlling downstream cell culture systems in accordance with the present disclosure.

In one embodiment, multiple systems as shown in FIG. 6 can operate in parallel to produce reference data for model controllers. For example, in one embodiment, the system can include multiple perfusion bioreactors and one or more input controllers that can vary one or more attribute influencing parameters within each of the bioreactors as the bioreactors are operated in parallel. For example, in one embodiment, the same attribute influencing parameter or parameters can be varied in two or more perfusion bioreactors operating in parallel. The attribute influencing parameter or parameters can be varied differently in each of the perfusion bioreactors in order to obtain information on the effect of the attribute influencing parameter or parameters on one or more quality attributes. The multiple perfusion bioreactors can operate automatically using one or more input controllers and various other controllers designed to remove samples from the perfusion bioreactor, analyze the samples, and automatically send the information to a system database. In this manner, a significant amount of information can be collected to show how various attribute influencing parameters affect various different quality attributes. Machine learning can be used to spot trends or other relationships that can then be used by model controllers in controlling cell culture systems, such as cell culture systems that operate in batch mode.

The devices, facilities and methods described herein are suitable for culturing any desired cell line including prokaryotic and/or eukaryotic cell lines. Further, in embodiments, the devices, facilities and methods are suitable for culturing suspension cells or anchorage-dependent (adherent) cells and are suitable for production operations configured for production of pharmaceutical and biopharmaceutical products—such as polypeptide products, nucleic acid products (for example DNA or RNA), or cells and/or viruses such as those used in cellular and/or viral therapies.

In embodiments, the cells express or produce a product, such as a recombinant therapeutic or diagnostic product. As described in more detail below, examples of products produced by cells include, but are not limited to, antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the devices, facilities and methods can be used for producing biosimilars.

As mentioned, in embodiments, devices, facilities and methods allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., proteins, peptides, antibiotics, amino acids, nucleic acids (such as DNA or RNA), synthesized by the eukaryotic cells in a large-scale manner. Unless stated otherwise herein, the devices, facilities, and methods can include any desired volume or production capacity including but not limited to bench-scale, pilot-scale, and full production scale capacities.

Moreover and unless stated otherwise herein, the devices, facilities, and methods can include any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermentor or fermentation unit, or any other reaction vessel and the term "reactor" is used interchangeably with "fermentor." For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and CO2 levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316L or any other suitable stainless steel) and Inconel, plastics, and/or glass.

In embodiments and unless stated otherwise herein, the devices, facilities, and methods described herein can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the devices, systems, and methods described herein can be housed and/or performed in a single location or facility or alternatively be housed and/or performed at separate or multiple locations and/or facilities.

By way of non-limiting examples and without limitation, U.S. Publication Nos. 2013/0280797; 2012/0077429; 2011/0280797; 2009/0305626; and U.S. Pat. Nos. 8,298,054; 7,629,167; and 5,656,491, which are hereby incorporated by reference in their entirety, describe example facilities, equipment, and/or systems that may be suitable.

In embodiments, the cells are eukaryotic cells, e.g., mammalian cells. The mammalian cells can be for example human or rodent or bovine cell lines or cell strains. Examples of such cells, cell lines or cell strains are e.g. mouse myeloma (NSO)-cell lines, Chinese hamster ovary (CHO)-cell lines, HT1080, H9, HepG2, MCF7, MDBK Jurkat, NIH3T3, PC12, BHK (baby hamster kidney cell), VERO, SP2/0, YB2/0, YO, C127, L cell, COS, e.g., COS1 and COS7, QC1-3,HEK-293, VERO, PER.C6, HeLA, EB1, EB2, EB3, oncolytic or hybridoma-cell lines. Preferably the mammalian cells are CHO-cell lines. In one embodiment, the cell is a CHO cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the Potelligent® CHOK1 SV (Lonza Biologics, Inc.). Eukaryotic cells can also be avian cells, cell lines or cell strains, such as for example, EBx® cells, EB14, EB24, EB26, EB66, or EBvl3.

In one embodiment, the eukaryotic cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In one embodiment, the cell is a differentiated form of any of the cells described herein. In one embodiment, the cell is a cell derived from any primary cell in culture.

In embodiments, the cell is a hepatocyte such as a human hepatocyte, animal hepatocyte, or a non-parenchymal cell. For example, the cell can be a plateable metabolism qualified human hepatocyte, a plateable induction qualified human hepatocyte, plateable Qualyst Transporter Certified™ human hepatocyte, suspension qualified human hepatocyte (including 10-donor and 20-donor pooled hepatocytes), human hepatic kupffer cells, human hepatic stellate cells, dog hepatocytes (including single and pooled Beagle hepatocytes), mouse hepatocytes (including CD-1 and C57Bl/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Example hepatocytes are commercially available from Triangle Research Labs, LLC, 6 Davis Drive Research Triangle Park, N.C., USA 27709.

In one embodiment, the eukaryotic cell is a lower eukaryotic cell such as e.g. a yeast cell (e.g., *Pichia* genus (e.g. *Pichia pastoris, Pichia methanolica, Pichia kluyveri*, and *Pichia angusta*), *Komagataella* genus (e.g. *Komagataella pastoris, Komagataella pseudopastoris* or *Komagataella phaffii*), *Saccharomyces* genus (e.g. *Saccharomyces cerevisae, cerevisiae, Saccharomyces kluyveri, Saccharomyces uvarum*), *Kluyveromyces* genus (e.g. *Kluyveromyces lactis, Kluyveromyces marxianus*), the *Candida* genus (e.g. *Candida utilis, Candida cacaoi, Candida boidinii,*), the *Geotrichum* genus (e.g. *Geotrichum fermentans*), *Hansenula polymorpha, Yarrowia lipolytica*, or *Schizosaccharomyces pombe*, Preferred is the species *Pichia pastoris*. Examples for *Pichia pastoris* strains are X33, GS115, KM71, KM71H; and CBS7435.

In one embodiment, the eukaryotic cell is a fungal cell (e.g. *Aspergillus* (such as *A. niger, A. fumigatus, A. orzyae, A. nidula*), *Acremonium* (such as *A. thermophilum*), *Chaetomium* (such as *C. thermophilum*), *Chrysosporium* (such as *C. thermophile*), *Cordyceps* (such as *C. militaris*), *Corynascus, Ctenomyces, Fusarium* (such as *F. oxysporum*), *Glomerella* (such as *G. graminicola*), *Hypocrea* (such as *H. jecorina*), *Magnaporthe* (such as *M. orzyae*), *Myceliopthora* (such as *M. thermophile*), *Nectria* (such as *N. heamatococca*), *Neurospora* (such as *N. crassa*), *Penicillium, Sporotrichum* (such as *S. thermophile*), *Thielavia* (such as *T. terrestris, T. heterothallica*), *Trichoderma* (such as *T. reesei*), or *Verticillium* (such as *V. dahlia*)).

In one embodiment, the eukaryotic cell is an insect cell (e.g., Sf9, Mimic™ Sf9, Sf21, High Five™ (BT1-TN-5B1-4), or BT1-Ea88 cells), an algae cell (e.g., of the genus Amphora, Bacillariophyceae, *Dunaliella, Chlorella, Chlamydomonas*, Cyanophyta (cyanobacteria), *Nannochloropsis, Spirulina*, or *Ochromonas*), or a plant cell (e.g., cells from monocotyledonous plants (e.g., maize, rice, wheat, or *Setaria*), or from a dicotyledonous plants (e.g., cassava, potato, soybean, tomato, tobacco, alfalfa, *Physcomitrella patens* or *Arabidopsis*).

In one embodiment, the cell is a bacterial or prokaryotic cell.

In embodiments, the prokaryotic cell is a Gram-positive cells such as *Bacillus, Streptomyces Streptococcus, Staphylococcus* or *Lactobacillus. Bacillus* that can be used is, e.g. the *B. subtilis, B. amyloliquefaciens, B. licheniformis, B. natto*, or *B. megaterium*. In embodiments, the cell is *B. subtilis*, such as *B. subtilis* 3NA and *B. subtilis* 168. *Bacillus* is obtainable from, e.g., the *Bacillus* Genetic Stock Center, Biological Sciences 556, 484 West 12th Avenue, Columbus Ohio 43210-1214.

In one embodiment, the prokaryotic cell is a Gram-negative cell, such as *Salmonella* spp. or *Escherichia coli*, such as e.g., TG1, TG2, W3110, DH1, DHB4, DH5a, HMS 174, HMS174 (DE3), NM533, C600, HB101, JM109, MC4100, XL1-Blue and Origami, as well as those derived from *E. coli* B-strains, such as for example BL-21 or BL21 (DE3), all of which are commercially available.

Suitable host cells are commercially available, for example, from culture collections such as the DSMZ (Deutsche Sammlung von Mikroorganismen and Zellkulturen GmbH, Braunschweig, Germany) or the American Type Culture Collection (ATCC).

In embodiments, the cultured cells are used to produce proteins e.g., antibodies, e.g., monoclonal antibodies, and/or recombinant proteins, for therapeutic use. In embodiments, the cultured cells produce peptides, amino acids, fatty acids or other useful biochemical intermediates or metabolites. For example, in embodiments, molecules having a molecular weight of about 4000 daltons to greater than about 140,000 daltons can be produced. In embodiments, these molecules can have a range of complexity and can include posttranslational modifications including glycosylation.

In embodiments, the protein is, e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-nl, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alpha, collagenase, carperitide, recombinant human epidermal growth factor (topical gel, wound healing), DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VIII, palifermin, Indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, Eutropin, KP-102 program, somatropin, mecasermin (growth failure), enlfavirtide, Org-33408, insulin glargine, insulin glulisine, insulin (inhaled), insulin lispro, insulin detemir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alpha, trafermin, ziconotide, taltirelin, diboterminalfa, atosiban, becaplerm in, eptifibatide, Zemaira, CTC-111, Shanvac-B, HPV vaccine (quadrivalent), octreotide, lanreotide, ancestirn, agalsidase beta, agalsidase alpha, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant Cl esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alpha-n3 (oral), belatacept, transdermal insulin patches, AMG-531, MBP-8298, Xerecept, opebacan, AIDSVAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMlD, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 131I-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, ACM-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutancous injection, eczema), pitrakinra (inhaled dry powder, asthma), Multikine, RG-1068, MM-093, NBI-6024, AT-001, PI-0824, Org-39141, Cpn10 (autoimmune diseases/inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alpha-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague FIV vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alphagalactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, *S pneumoniae* pediatric vaccine, malaria vaccine, *Neisseria meningitidis* Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

In some embodiments, the polypeptide is adalimumab (HUMIRA), infliximab (REMICADE™), rituximab (RITUXAN™/MAB THERA™) etanercept (ENBREL™), bevacizumab (AVASTIN™), trastuzumab (HERCEPTIN™), pegrilgrastim (NEULASTA™), or any other suitable polypeptide including biosimilars and biobetters.

Other suitable polypeptides are those listed below and in Table 1 of US2016/0097074:

TABLE I

| Protein Product | Reference Listed Drug |
| --- | --- |
| interferon gamma-1b | Actimmune ® |
| alteplase; tissue plasminogen activator | Activase ®/Cathflo ® |
| Recombinant antihemophilic factor | Advate |
| human albumin | Albutein ® |
| Laronidase | Aldurazyme ® |
| Interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| Bivalirudin | Angiomax ® |
| darbepoetin alfa | Aranesp ™ |
| Bevacizumab | Avastin ™ |
| interferon beta-1a; recombinant | Avonex ® |
| coagulation factor IX | BeneFix ™ |
| Interferon beta-1b | Betaseron ® |
| Tositumomab | BEXXAR ® |
| antihemophilic factor | Bioclate ™ |
| human growth hormone | BioTropin ™ |
| botulinum toxin type A | BOTOX ® |
| Alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune fab [ovine] | DigiFab ™ |
| Rasburicase | Elitek ® |
| Etanercept | ENBREL ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | FORTEO ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | HEMOFIL |
| adefovir dipivoxil | Hepsera ™ |
| Trastuzumab | Herceptin ® |
| Insulin | Humalog ® |
| antihemophilic factor/von Willebrand factor complex-human | Humate-P ® |
| Somatotropin | Humatrope ® |
| Adalimumab | HUMIRA ™ |
| human insulin | Humulin ® |
| recombinant human hyaluronidase | Hylenex ™ |
| interferon alfacon-1 | Infergen ® |
| eptifibatide | Integrilin ™ |
| alpha-interferon | Intron A ® |
| Palifermin | Kepivance |
| Anakinra | Kineret ™ |
| antihemophilic factor | Kogenate ® FS |
| insulin glargine | Lantus ® |
| granulocyte macrophage colony-stimulating factor | Leukine ®/ Leukine ® Liquid |
| lutropin alfa for injection | Luveris |
| OspA lipoprotein | LYMErix ™ |
| Ranibizumab | LUCENTIS ® |
| gemtuzumab ozogamicin | Mylotarg ™ |
| Galsulfase | Naglazyme ™ |
| Nesiritide | Natrecor ® |
| Pegfilgrastim | Neulasta ™ |
| Oprelvekin | Neumega ® |
| Filgrastim | Neupogen ® |
| Fanolesomab | NeutroSpec ™ (formerly LeuTech ®) |
| somatropin [rDNA] | Norditropin ®/Norditropin Nordiflex ® |
| Mitoxantrone | Novantrone ® |
| insulin; zinc suspension; | Novolin L ® |
| insulin; isophane suspension | Novolin N ® |
| insulin, regular; | Novolin R ® |
| Insulin | Novolin ® |
| coagulation factor VIIa | NovoSeven ® |
| Somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| high-molecular weight hyaluronan | Orthovisc ® |
| human chorionic gonadotropin | Ovidrel ® |
| live attenuated *Bacillus* Calmette-Guerin | Pacis ® |
| peginterferon alfa-2a | Pegasys ® |
| pegylated version of interferon alfa-2b | PEG-Intron ™ |
| Abarelix (injectable suspension); gonadotropin-releasing hormone antagonist | Plenaxis ™ |
| epoietin alfa | Procrit ® |
| Aldesleukin | Proleukin, IL-2 ® |
| Somatrem | Protropin ® |
| dornase alfa | Pulmozyme ® |
| Efalizumab; selective, reversible T-cell blocker | RAPTIVA ™ |
| combination of ribavirin and alpha interferon | Rebetron ™ |
| Interferon beta 1a | Rebif ® |
| antihemophilic factor | Recombinate ® rAHF/ |
| antihemophilic factor | ReFacto ® |
| Lepirudin | Refludan ® |
| Infliximab | REMICADE ® |
| Abciximab | ReoPro ™ |
| Reteplase | Retavase ™ |
| Rituxima | Rituxan ™ |

TABLE I-continued

| Protein Product | Reference Listed Drug |
|---|---|
| interferon alfa-2$^a$ | Roferon-A ® |
| Somatropin | Saizen ® |
| synthetic porcine secretin | SecreFlo ™ |
| Basiliximab | Simulect ® |
| Eculizumab | SOLIRIS (R) |
| Pegvisomant | SOMAVERT ® |
| Palivizumab; recombinantly produced, humanized mAb | Synagis ™ |
| thyrotropin alfa | Thyrogen ® |
| Tenecteplase | TNKase ™ |
| Natalizumab | TYSABRI ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |
| Somatotropin | Zorbtive ™ (Serostim ®) |

In embodiments, the polypeptide is a hormone, blood clotting/coagulation factor, cytokine/growth factor, antibody molelcule, fusion protein, protein vaccine, or peptide as shown in Table 2.

TABLE 2

Exemplary Products

| Therapeutic Product type | Product | Trade Name |
|---|---|---|
| Hormone | Erythropoietin, Epoein-α | Epogen, Procrit |
| | Darbepoetin-α | Aranesp |
| | Growth hormone (GH), somatotropin | Genotropin, Humatrope, Norditropin, NovIVitropin, Nutropin, Omnitrope, Protropin, Siazen, Serostim, Valtropin |
| | Human follicle-stimulating hormone (FSH) | Gonal-F, Follistim |
| | Human chorionic gonadotropin | Ovidrel |
| | Lutropin-α | Luveris |
| | Glucagon | GlcaGen |
| | Growth hormone releasing hormone (GHRH) | Geref |
| | Secretin | ChiRhoStim (human peptide), SecreFlo (porcine peptide) |
| | Thyroid stimulating hormone (TSH), thyrotropin | Thyrogen |
| Blood Clotting/Coagulation Factors | Factor VIIa | NovoSeven |
| | Factor VIII | Bioclate, Helixate, Kogenate, Recombinate, ReFacto |
| | Factor IX | Benefix |
| | Antithrombin III (AT-III) | Thrombate III |
| | Protein C concentrate | Ceprotin |
| Cytokine/Growth factor | Type I alpha-interferon | Infergen |
| | Interferon-αn3 (IFNαn3) | Alferon N |
| | Interferon-β1a (rIFN- β) | Avonex, Rebif |
| | Interferon-β1b (rIFN- β) | Betaseron |
| | Interferon-γ1b (IFN γ) | Actimmune |
| | Aldesleukin (interleukin 2(IL2), epidermal theymocyte activating factor; ETAF | Proleukin |
| | Palifermin (keratinocyte growth factor; KGF) | Kepivance |
| | Becaplemin (platelet-derived growth factor; PDGF) | Regranex |
| | Anakinra (recombinant IL1 antagonist) | Anril, Kineret |
| Antibody molecules | Bevacizumab (VEGFA mAb) | Avastin |
| | Cetuximab (EGFR mAb) | Erbitux |
| | Panitumumab (EGFR mAb) | Vectibix |
| | Alemtuzumab (CD52 mAb) | Campath |
| | Rituximab (CD20 chimeric Ab) | Rituxan |
| | Trastuzumab (HER2/Neu mAb) | Herceptin |
| | Abatacept (CTLA Ab/Fc fusion) | Orencia |
| | Adalimumab (TNFα mAb) | Humira |
| | Etanercept (TNF | Enbrel |
| | | Remicade |
| | | Amevive |
| | | Raptiva |
| | | Tysabri |
| | | Soliris |
| | | Orthoclone, OKT3 |

TABLE 2-continued

| Exemplary Products | | |
|---|---|---|
| Therapeutic Product type | Product | Trade Name |
| | receptor/Fc fusion) | |
| | Infliximab (TNFα chimeric mAb) | |
| | Alefacept (CD2 fusion protein) | |
| | Efalizumab (CD11a mAb) | |
| | Natalizumab (integrin α4 subunit mAb) | |
| | Eculizumab (C5mAb) | |
| | Muromonab-CD3 | |
| Other: Fusion proteins/Protein vaccines/Peptides | Insulin | Humulin, Novolin |
| | Hepatitis B surface antigen (HBsAg) | Engerix, Recombivax HB |
| | HPV vaccine | Gardasil |
| | OspA | LYMErix |
| | Anti-Rhesus(Rh) immunoglobulin G | Rhophylac |
| | Enfuvirtide | Fuzeon |
| | Spider silk, e.g., fibrion | QMONOS |

In embodiments, the protein is multispecific protein, e.g., a bispecific antibody as shown in Table 3.

TABLE 3

| Bispecific Formats | | | | | |
|---|---|---|---|---|---|
| Name (other names, sponsoring organizations) | BsAb format | Targets | Proposed mechanisms of action | Development stages | Diseases (or healthy volunteers) |
| Catumaxomab (Removab ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3, HER2 | Retargeting of T cells to tumor | Phase I/II | Advanced solid tumors |
| Blinatumomab (Blincyto ®, AMG 103, MT 103, MEDI 538, Amgen) | BiTE | CD3, CD19 | Retargeting of T cells to tumor | Approved in USA Phase II and III Phase II Phase I | Precursor B-cell ALL ALL DLBCL NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |
| MGD007 (Macrogenics) | DART | CD3, gpA33 | Retargeting of T cells to tumor | Phase I | Colorectal cancer |
| MGD011 (Macrogenics) | DART | CD19, CD3 | | | |
| SCORPION (Emergent Biosolutions, Trubion) | BsAb | CD3, CD19 | Retargeting of T cells to tumor | | |

TABLE 3-continued

| Bispecific Formats | | | | | |
|---|---|---|---|---|---|
| Name (other names, sponsoring organizations) | BsAb format | Targets | Proposed mechanisms of action | Development stages | Diseases (or healthy volunteers) |
| AFM11 (Affimed Therapeutics) | TandAb | CD3, CD19 | Retargeting of T cells to tumor | Phase I | NHL and ALL |
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T-cells (Barbara Ann Karmanos Cancer Institute) | T cells preloaded with BsAb | CD3, EGFR | Autologous activated T cells to EGFR-positive tumor | Phase I | Colon and pancreatic cancers |
| rM28 (University Hospital Tübingen) | Tandem scFv | CD28, MAPG | Retargeting of T cells to tumor | Phase II | Metastatic melanoma |
| IMCgp100 (Immunocore) | ImmTAC | CD3, peptide MHC | Retargeting of T cells to tumor | Phase I/II | Metastatic melanoma |
| DT2219ARL (NCI, University of Minnesota) | 2 scFv linked to diphtheria toxin | CD19, CD22 | Targeting of protein toxin to tumor | Phase I | B cell leukemia or lymphoma |
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |
| MM-111 (Merrimack Pharmaceuticals) | HSA body | HER2, HER3 | Blockade of 2 receptors | Phase II Phase I | Gastric and esophageal cancers Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGF A | Blockade of 2 proangiogenics | Phase I | Solid tumors |
| RG7716 (Roche) | CrossMab | Ang2, VEGF A | Blockade of 2 proangiogenics | Phase I | Wet AMD |
| OMP-305B83 (OncoMed) | BsAb | DLL4/VEGF | | | |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-1β | Blockade of 2 proinflammatory cytokines | Phase II | Osteoarthritis |
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase I/II | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |
| GSK2434735 (GSK) | Dual-targeting domain | IL-13, IL-4 | Blockade of 2 proinflammatory cytokines | Phase I | (Healthy volunteers) |
| Ozoralizumab (ATN103, Ablynx) | Nanobody | TNF, HSA | Blockade of proinflammatory cytokine, binds to HSA to increase half-life | Phase II | Rheumatoid arthritis |
| ALX-0761 (Merck Serono, Ablynx) | Nanobody | IL-17A/F, HSA | Blockade of 2 proinflammatory cytokines, binds to HSA to increase half-life | Phase I | (Healthy volunteers) |
| ALX-0061 (AbbVie, Ablynx; | Nanobody | IL-6R, HSA | Blockade of proinflammatory cytokine, binds to HSA to increase half-life | Phase I/II | Rheumatoid arthritis |
| ALX-0141 (Ablynx, Eddingpharm) | Nanobody | RANKL, HSA | Blockade of bone resorption, binds to HSA to increase half-life | Phase I | Postmenopausal bone loss |
| RG6013/ACE910 (Chugai, Roche) | ART-Ig | Factor IXa, factor X | Plasma coagulation | Phase II | Hemophilia |

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A process for creating reference data for predicting quality attribute values in a cell culture comprising;
   introducing a cell culture into a perfusion bioreactor;
   feeding a nutrient media to the perfusion bioreactor and withdrawing fluid media from the perfusion bioreactor;
   controlling a plurality of attribute influencing parameters in the perfusion bioreactor, the plurality of attribute influencing parameters having an impact on at least a first quality attribute in the cell culture, the plurality of attribute influencing parameters being controlled in the perfusion bioreactor in a manner so that the plurality of attribute influencing parameters in the perfusion bioreactor vary over time;
   determining a quantity of the first quality attribute over time in the cell culture as the plurality of attribute influencing parameters are changed;
   determining a quantity of a second quality attribute over time in the cell culture also as the plurality of attribute influencing parameters are changed; and
   wherein a first attribute influencing parameter and a second attribute influencing parameter are changed within the perfusion bioreactor in a step wise manner;
   wherein after each step wise change of the first attribute influencing parameter, the first quality attribute attains steady state within the perfusion bioreactor before a further step wise change is made and wherein after each step wise change of the second attribute influencing parameter, the second quality attribute attains steady state within the perfusion bioreactor before a further steep wise change is made;
   wherein the determined quantity of the first quality attribute over time and the determined second quality attribute quantity over time comprise reference data and wherein the process further comprises collecting the reference data in a manner so that the reference data is configured to be inputted into a controller that predicts future quantities of the first and second quality attributes over time in a downstream cell culture process, wherein the first and second quality attributes are selected from the group consisting of lactate, protein, glycan, a charge variant, an aggregate, disulfide oxidation, fragmentation, disulfide reduction, methionine oxidation, lysine variant, bispecific monoclonal antibody heterology, sequence variant, un-coded amino acid substitution, ammonia, viable cell density, cell size, cell viability, alanine, glutamine, and a disulfide shuffling variant, wherein the plurality of attribute influencing parameters are selected from the group consisting of pH, glutamate concentration, glucose concentration, asparagine concentration, temperature, mannose concentration, galactose concentration, N-acetyl mannosamine concentration, sucrose concentration, lysine concentration, methionine concentration, serine concentration, lipid concentration, vitamin concentration, manganese concentration, copper concentration, iron concentration, selenium concentration, dissolved oxygen, applied shear rate and nutrient feed rate.

2. The process as defined in claim 1, comprising the steps of: controlling at least three attribute influencing parameters in the perfusion bioreactor, the at least three attribute influencing parameters having an impact on the second quality attribute in the cell culture, the at least three attribute influencing parameters being controlled in the perfusion bioreactor in a manner so that at least three attribute influencing parameters in the bioreactor vary over time, wherein after each step wise change of a third attribute influencing parameter, a third quality attribute attains steady state within the perfusion bioreactor before a further step wise change is made.

3. The process as defined in claim 1, wherein the quantity of the first quality attribute and the quantity of the second quality attribute are determined simultaneously.

4. The process as defined in claim 1, wherein the reference data is configured to be inputted into a predictive model, the predictive model using the reference data to determine future concentrations of the first and second quality attributes in a second bioreactor of a downstream cell culture process.

5. The process as defined in claim 4, wherein the cell culture is propagated in a batch process.

6. The process as defined in claim 2, wherein the at least three attribute influencing parameters are fed to the perfusion bioreactor simultaneously.

7. The process as defined in claim 1, wherein the cell culture in the perfusion bioreactor has a cell density and wherein the cell density remains constant during the process.

8. The process as defined in claim 1, wherein the volume within the perfusion bioreactor remains constant during the process.

9. The process as defined in claim 1, wherein the reference data are collected during a period of time less than 48 hours from the perfusion bioreactor.

10. The process as defined in claim 2, wherein the at least three attribute influencing parameters are changed within the perfusion bioreactor in a sinusoidal manner.

11. The process as defined in claim 4, further comprising the steps of: determining a quantity of at least the first quality attribute in a cell culture; sending the quality attribute quantity to a controller, the controller including the predictive model that determines a future quantity of the quality attribute in the cell culture; and selectively changing at least one condition within the cell culture based upon the determined future quantity of the quality attribute in the cell culture for maintaining the quality attribute quantity within preset limits.

12. The process as defined in claim 11, wherein the cell culture is propagated in a batch process.

13. The process as defined in claim 1, wherein the cell culture comprises mammalian cells.

14. The process as defined in claim 1, wherein at least the first quality attribute is lactate, glycan, a charge variant, disulfide oxidation, disulfide reduction, methionine oxidation, lysine variant, ammonia, viable cell density, cell size, cell viability, alanine, glutamine, or a disulfide shuffling variant.

15. The process as defined in claim 1, wherein the plurality of attribute influencing parameters are pH, glutamate concentration, glucose concentration, asparagine concentration, temperature, mannose concentration, galactose concentration, N-acetyl mannosamine concentration, sucrose concentration, lysine concentration, methionine concentration, serine concentration, lipid concentration, vitamin concentration, manganese concentration, dissolved oxygen, or nutrient feed rate.

16. The process as defined in claim 1, wherein the determined quantity of the first quality attribute over time comprises a concentration of the first quality attribute over time and wherein the determined quantity of the second quality attribute over time comprises the concentration of the second quality attribute over time.

17. A process for creating reference data for predicting quality attribute values in a cell culture comprising;
introducing a cell culture into a perfusion bioreactor;
feeding a nutrient media to the perfusion bioreactor and withdrawing fluid media from the perfusion bioreactor;
controlling a plurality of attribute influencing parameters in the perfusion bioreactor, the plurality of attribute influencing parameters having an impact on at least a first quality attribute in the cell culture, the plurality of attribute influencing parameters being controlled in the perfusion bioreactor in a manner so that the plurality of attribute influencing parameters in the perfusion bioreactor vary over time;
determining a quantity of the first quality attribute over time in the cell culture as the plurality of attribute influencing parameters are changed;
determining a quantity of a second quality attribute over time in the cell culture also as the plurality of attribute influencing parameters are changed; and
wherein a first attribute influencing parameter and a second attribute influencing parameter are changed within the perfusion bioreactor in a step wise manner;
wherein after each step wise change of the first attribute influencing parameter, the first quality attribute does not attain steady state within the perfusion bioreactor before a further step wise change is made and wherein after each step wise change of the second attribute influencing parameter, the second quality attribute does not attain steady state within the perfusion bioreactor before a further step wise change is made;
wherein the determined quantity of the first quality attribute over time and the determined second quality attribute quantity over time comprise reference data and wherein the process further comprises collecting the reference data in a manner so that the reference data is configured to be inputted into a controller that predicts future quantities of the first and second quality attributes over time in a downstream cell culture process,
wherein the first and second quality attributes are selected from the group consisting of lactate, protein, glycan, a charge variant, an aggregate, disulfide oxidation, fragmentation, disulfide reduction, methionine oxidation, lysine variant, bispecific monoclonal antibody heterology, sequence variant, un-coded amino acid substitution, ammonia, viable cell density, cell size, cell viability, alanine, glutamine, and a disulfide shuffling variant, wherein the plurality of attribute influencing parameters are selected from the group consisting of pH, glutamate concentration, glucose concentration, asparagine concentration, temperature, mannose concentration, galactose concentration, N-acetyl mannosamine concentration, sucrose concentration, lysine concentration, methionine concentration, serine concentration, lipid concentration, vitamin concentration, manganese concentration, copper concentration, iron concentration, selenium concentration, dissolved oxygen, applied shear rate and nutrient feed rate.

18. The process as defined in claim 17, comprising the steps of: controlling at least three attribute influencing parameters in the perfusion bioreactor, the at least three attribute influencing parameters having an impact on the second quality attribute in the cell culture, the at least three attribute influencing parameters being controlled in the perfusion bioreactor in a manner so that at least three attribute influencing parameters in the bioreactor vary over time,
wherein after each step wise change of a third attribute influencing parameter, a third quality attribute attains steady state within the perfusion bioreactor before a further step wise change is made.

19. A process as defined in claim 17, wherein the quantity of the first quality attribute and the quantity of the second quality attribute are determined simultaneously.

20. A process as defined in claim 17, wherein the reference data is configured to be inputted into a predictive model, the predictive model using the reference data to determine future concentrations of the first and second quality attributes in a second bioreactor of a downstream cell culture process.

21. A process as defined in claim 20, wherein the cell culture is propagated in a batch process.

22. A process as defined in claim 18, wherein the at least three attribute influencing parameters are fed to the perfusion bioreactor simultaneously.

23. A process as defined in claim 17, wherein the cell culture in the perfusion bioreactor has a cell density and wherein the cell density remains constant during the process.

24. A process as defined in claim 17, wherein the volume within the perfusion bioreactor remains constant during the process.

25. A process as defined in claim 17, wherein the reference data are collected during a period of time less than 48 hours from the perfusion bioreactor.

26. A process as defined in claim 18, wherein the at least three attribute influencing parameters are changed within the perfusion bioreactor in a sinusoidal manner.

27. A process as defined in claim 20, further comprising the steps of: determining a quantity of at least the first quality attribute in a cell culture; sending the quality attribute quantity to a controller, the controller including the predictive model that determines a future quantity of the quality attribute in the cell culture; and selectively changing at least one condition within the cell culture based upon the determined future quantity of the quality attribute in the cell culture for maintaining the quality attribute quantity within preset limits.

28. A process as defined in claim 27, wherein the cell culture is propagated in a batch process.

29. A process as defined in claim 17, wherein the cell culture comprises mammalian cells.

30. A process as defined in claim 17, wherein at least the first quality attribute is lactate, glycan, a charge variant, disulfide oxidation, disulfide reduction, methionine oxidation, lysine variant, ammonia, viable cell density, cell size, cell viability, alanine, glutamine, or a disulfide shuffling variant.

31. A process as defined in claim 17, wherein the plurality of attribute influencing parameters are pH, glutamate concentration, glucose concentration, asparagine concentration, temperature, mannose concentration, galactose concentration, N-acetyl mannosamine concentration, sucrose concentration, lysine concentration, methionine concentration, serine concentration, lipid concentration, vitamin concentration, manganese concentration, dissolved oxygen, or nutrient feed rate.

32. A process as defined in claim 17, wherein the determined quantity of the first quality attribute over time comprises a concentration of the first quality attribute over time and wherein the determined quantity of the second quality attribute over time comprises the concentration of the second quality attribute over time.

* * * * *